United States Patent
Pikul et al.

(10) Patent No.: US 6,696,456 B1
(45) Date of Patent: Feb. 24, 2004

(54) BETA DISUBSTITUTED METALLOPROTEASE INHIBITORS

(75) Inventors: Stanislaw Pikul, Germantown, MD (US); Norman Eugene Ohler, Germantown, MD (US); Kelly Michelle Solinsky, Cincinnati, OH (US); Neil Gregory Almstead, Warren, NJ (US); Biswanath De, Cincinnati, OH (US); Michael George Natchus, Glendale, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/687,681

(22) Filed: Oct. 13, 2000

Related U.S. Application Data

(60) Provisional application No. 60/159,320, filed on Oct. 14, 1999.

(51) Int. Cl.[7] ............... C07D 213/70; C07D 239/38; C07D 277/36; A61K 31/18; A61K 31/505
(52) U.S. Cl. ............... 514/274; 514/351; 514/352; 514/357; 514/367; 514/369; 514/376; 514/384; 514/398; 544/332; 546/300; 546/312; 546/335; 546/337; 548/187; 548/170; 548/229; 548/264.4; 548/324.1; 562/430
(58) Field of Search ............... 514/562, 274, 514/351, 352, 369, 357, 367, 376, 384, 398; 562/430; 544/332; 546/300, 312, 335, 337; 548/187, 170, 229, 264.4, 324.1

(56) References Cited

U.S. PATENT DOCUMENTS

| | | | |
|---|---|---|---|
| 4,743,587 A | 5/1988 | Dickens et al. | 514/575 |
| 4,771,038 A | 9/1988 | Wolanin et al. | 514/18 |
| 4,885,283 A | 12/1989 | Broadhurst et al. | 514/78 |
| 4,996,358 A | 2/1991 | Handa et al. | 562/621 |
| 5,183,900 A | 2/1993 | Galardy et al. | 548/495 |
| 5,300,674 A | 4/1994 | Crimmin et al. | 560/42 |
| 5,318,964 A | 6/1994 | Broadhurst et al. | 514/228.2 |
| 5,387,610 A | 2/1995 | Gray et al. | 514/575 |
| 5,403,952 A | 4/1995 | Hagmann et al. | 510/85 |
| 5,442,110 A | 8/1995 | Isomura et al. | 562/621 |
| 5,470,834 A | 11/1995 | Schwartz et al. | 514/19 |
| 5,506,242 A | 4/1996 | MacPherson et al. | 514/336 |
| 5,545,735 A | 8/1996 | Bochis et al. | 540/490 |
| 5,614,625 A | 3/1997 | Broadhurst et al. | 540/480 |
| 5,618,844 A | 4/1997 | Gowravaram et al. | 514/575 |
| 5,665,753 A | 9/1997 | Frazee et al. | 514/394 |
| 5,691,382 A | 11/1997 | Crimmin et al. | 514/575 |
| 5,714,491 A | 2/1998 | Morphy et al. | 514/256 |
| 5,747,514 A | 5/1998 | Beckett et al. | 514/352 |
| 5,753,653 A * | 5/1998 | Bender et al. | 514/227.5 |
| 5,763,621 A | 6/1998 | Beckett et al. | 549/65 |
| 5,773,438 A | 6/1998 | Levy et al. | 514/237.8 |
| 5,827,890 A | 10/1998 | Beeley et al. | 514/575 |
| 5,853,623 A | 12/1998 | Montana et al. | 260/998.2 |
| 5,861,436 A | 1/1999 | Beckett et al. | 514/575 |
| 5,872,152 A | 2/1999 | Brown et al. | 514/575 |
| 5,902,791 A | 5/1999 | Beckett et al. | 514/19 |
| 5,962,529 A | 10/1999 | Miller et al. | 514/575 |
| 5,985,900 A * | 11/1999 | Bender et al. | 514/336 |
| 6,022,898 A | 2/2000 | Miller et al. | 514/576 |
| 6,028,110 A | 2/2000 | Miller et al. | 514/575 |
| 6,066,662 A | 5/2000 | Broadhurst et al. | 514/384 |
| 6,093,398 A | 7/2000 | Khaw et al. | 424/146.1 |
| 6,114,435 A | 9/2000 | Nilz et al. | 524/548 |
| 6,225,311 B1 * | 5/2001 | Levin et al. | 514/227.5 |

FOREIGN PATENT DOCUMENTS

| | | | |
|---|---|---|---|
| EP | 0575844 B1 | 1/1998 | C07C/259/06 |
| EP | 0967201 A1 | 12/1999 | C07C/311/02 |
| GB | 2268934 A | 1/1994 | C07C/259/06 |
| JP | 07304770 A | 11/1995 | C07D/403/04 |
| JP | 08053403 A | 2/1996 | C07C/259/06 |
| WO | WO 92/17460 | 10/1992 | C07D/245/02 |

(List continued on next page.)

OTHER PUBLICATIONS

Mullins et al., "The Role of Proteinases in Cellular Invasiveness", *Biochimica et Biophysica Acta*, vol. 695, pp. 177–214 (1983).

Reich et al., "Effects of Inhibitors of Plasminogen Activator, Serine Proetinases, and Collagenase IV on the Invasion of Basement Membranes by Metastatic Cells", *Cancer Research*, Vol 48, pp. 3307–3312 (1988).

Henderson et al. "Design of Inhibitors of Articular Cartilage Destruction", *Drugs of the Future*, vol. 15, No. 5, pp. 495–508 (1990).

(List continued on next page.)

*Primary Examiner*—Deepak Rao
(74) *Attorney, Agent, or Firm*—David V. Upite; James C. Kellerman; Carl J. Roof

(57) ABSTRACT

Disclosed are compounds which are inhibitors of metalloproteases and which are effective in treating conditions characterized by excess activity of these enzymes. In particular, the compounds have a structure according to the following Formula (I):

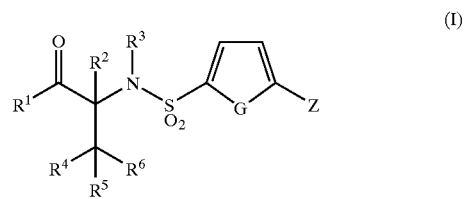

where $R^1$, $R^2$, $R^3$, $R^4$, $R^5$, $R^6$, G and Z have the meanings described in the specification. This invention also includes optical isomers, diastereomers and enantiomers of Formula I, and pharmaceutically-acceptable salts, biohydrolyzable amides, esters, and imides thereof. Also described are pharmaceutical compositions comprising these compounds, and methods of treating metalloprotease-related maladies using the compounds or the pharmaceutical compositions.

15 Claims, No Drawings

FOREIGN PATENT DOCUMENTS

| WO | WO 93/14112 | 7/1993 | ............ C07K/5/00 |
| --- | --- | --- | --- |
| WO | WO 94/00119 | 1/1994 | .......... A61K/31/40 |
| WO | WO 94/25432 | 11/1994 | ......... C07C/323/60 |
| WO | WO 95/12603 | 5/1995 | ............. C07F/9/30 |
| WO | WO 95/29892 | 11/1995 | ....... C07D/207/327 |
| WO | WO 95/33731 | 12/1995 | ......... C07D/237/04 |
| WO | WO 96/00214 | 1/1996 | ......... C07D/213/42 |
| WO | WO 98/39313 | 9/1998 | ......... C07D/295/14 |
| WO | WO 98/39329 | 9/1998 | ......... C07D/413/12 |
| WO | WO 98/43963 | * 10/1998 | |
| WO | WO 99/06340 | * 2/1999 | |
| WO | WO 99/41246 | 8/1999 | ......... C07D/285/36 |
| WO | WO 00/51975 | 9/2000 | ......... C07C/311/19 |
| WO | WO 00/51993 | 9/2000 | ......... C07D/277/00 |
| WO | WO 00/51993 A3 | 9/2000 | ......... C07D/277/36 |

OTHER PUBLICATIONS

Bird et al., "Synthesis of Novel N–Phosphonalkyl Dipeptide Inhibitors of Human Collagenase", *J. Med. Chem.*, vol. 37, pp. 158–169 (1994).

Wolfsberg et al., "ADAM, a Novel Family of Membrane Proteins Containing A Disintegrin And Metalloprotease Domain: Multipotential Functions in Cell–Cell and Cell–Matrix Ineractions", *The J. of Cell Biology*, vol. 131, No. 2, pp. 275–278 (1995).

Gijbels et al., "Reversal of Experimental Autoimmune Encephalomyelitis with a Hydroxamate Inhibitor of Matrix Metalloprotease", *J. Clin. Invest.*, vol. 94, pp. 2177–2182 (1994).

Yu et al., "Matrix Metalloproteinases, Novel Targets for Direct Cancer Therapy", *Clinical Pharmacology*, vol. 3, pp. 229–244 (1997).

Chanbers et al., "Changing Views of the Role of Matrix Metalloproteinases in Metastasis", *J. of the National Cancer Institute*, vol. 89, No. 17, pp. 1260–1270 (1997).

Bramhall, "The Matrix of Metalloproteinases and Their Inhibitors in Pancreatic Cancer", *International J. of Pancreatology*, vol. 21, No. 1, pp 1–12 (1997).

Rasmussen et al., "Matrix Metalloproteinase Ihnibition as a Novel Anticancer Strategy: A Review with Special Focus on Batimastat and Marimastat", *Pharmacol Ther.*, vol. 75, No. 1, pp. 69–75 (1997).

Nemunaitis et al., "Combined Analysis of Studies of the Effects of the Matrix Metalloproteinase Inhibitor Marimastat on Serum Tumor Markers in Advanced Cancer: Selcetion of a Biologically Active and tolerable Dose for Longer–Term Studies", *Clinical Cancer Research*, vol. 4, pp. 1101–1109 (1998).

* cited by examiner

BETA DISUBSTITUTED METALLOPROTEASE INHIBITORS

CROSS REFERENCE TO RELATED APPLICATION

This application claims the benefit of U.S. Provisional Application No. 60/159,320 filed Oct. 14, 1999.

TECHNICAL FIELD

This invention is directed to compounds that are useful in treating diseases associated with metalloprotease activity, particularly zinc metalloprotease activity. The invention is also directed to pharmaceutical compositions comprising the compounds, and to methods of treating metalloprotease-related maladies using the compounds or the pharmaceutical compositions.

BACKGROUND

A number of structurally related metalloproteases effect the breakdown of structural proteins. These metalloproteases often act on the intercellular matrix, and thus are involved in tissue breakdown and remodeling. Such proteins are referred to as metalloproteases or MPs.

There are several different families of MPs, classified by sequence homology, disclosed in the art. These MPs include Matrix-Metallo Proteases (MMPs); zinc metalloproteases; many of the membrane bound metalloproteases; TNF converting enzymes; angiotensin-converting enzymes (ACEs); disintegrins, including ADAMs (See Wolfsberg et al, 131 *J. Cell Bio.* 275–78 October, 1995); and the enkephalinases. Examples of MPs include human skin fibroblast collagenase, human skin fibroblast gelatinase, human sputum collagenase, aggrecanse and gelatinase, and human stromelysin. Collagenases, stromelysin, aggrecanase and related enzymes are thought to be important in mediating the symptomatology of a number of diseases.

Potential therapeutic indications of MP inhibitors have been discussed in the literature. See, for example, U.S. Pat. No. 5,506,242 (Ciba Geigy Corp.) and U.S. Pat. No. 5,403,952 (Merck & Co.); the following PCT published application: WO 96/06074 (British Bio Tech Ltd.); WO 96/00214 (Ciba Geigy), WO 95/35275 (British Bio Tech Ltd.), WO 95/35276 (British Bio Tech Ltd.), WO 95/33731 (Hoffman-LaRoche), WO 95/33709 (Hoffman-LaRoche), WO 95/32944 (British Bio Tech Ltd.), WO 95/26989 (Merck), WO 9529892 (DuPont Merck), WO 95/24921 (Inst. Opthamology), WO 95/23790 (SmithKline Beecham), WO 95/22966 (Sanofi Winthrop), WO 95/19965 (Glycomed), WO 95 19956 (British Bio Tech Ltd), WO 95/19957 (British Bio Tech Ltd.), WO 95/19961 (British Bio Tech Ltd.), WO 95/13289 (Chiroscience Ltd.), WO 95/12603 (Syntex), WO 95/09633 (Florida State Univ.), WO 95/09620 (Florida State Univ.), WO 95/04033 (Celitech), WO 94/25434 (Celltech), WO 94/25435 (Celltech); WO 93/14112 (Merck), WO 94/0019 (Glaxo), WO 93/21942 (British Bio Tech Ltd.), WO 92/22523 (Res. Corp. Tech Inc.), WO 94/10990 (British Bio Tech Ltd.), WO 93/09090 (Yamanouchi); British patents GB 2282598 (Merck) and GB 2268934 (British Bio Tech Ltd.); published European Patent Applications EP 95/684240 (Hoffman LaRoche), EP 574758 (Hoffman LaRoche) and EP 575844 (Hoffman LaRoche); published Japanese applications JP 08053403 (Fujusowa Pharm. Co. Ltd.) and JP 7304770 (Kanebo Ltd.); and Bird et al., *J. Med. Chem.*, vol. 37, pp. 158–69 (1994).

Examples of potential therapeutic uses of MP inhibitors include rheumatoid arthritis—Mullins, D. E., et al., *Biochim. Biophys. Acta.* (1983) 695:117–214; osteoarthritis—Henderson, B., et al., *Drugs of the Future* (1990) 15:495–508; cancer—Yu, A. E. et al., Matrix Metalloproteinases—Novel Targets for Directed Cancer Therapy, *Drugs & Aging*, Vol. 11(3), p. 229–244 (September 1997), Chambers, A. F. and Matrisian, L. M., Review: Changing Views of the Role of Matrix Metalloproteinases in Metastasis, *J. of the Nat'l Cancer Inst.*, Vol. 89(17), p. 1260–1270 (September 1997), Bramhall, S. R., The Matrix Metalloproteinases and Their Inhibitors in Pancreatic Cancer, *Internat'l J. of Pancreatology*, Vol. 4, p. 1101–1109 (May 1998), Nemunaitis, J. et al., Combined Analysis of Studies of the Effects of the Matrix Metalloproteinase Inhibitor Marimastat on Serum Tumor Markers in Advanced Cancer: Selection of a Biologically Active and Tolerable Dose for Longer-term Studies, *Clin. Cancer Res.*, Vol 4, p. 1101–1109 (May 1998), and Rasmussen, H. S. and McCann, P. P, Matrix Metalloproteinase Inhibition as a Novel Anticancer Strategy: A Review with Special Focus on Batimastat and Marimastat, *Pharmacol. Ther.*, Vol 75(1), p. 69–75 (1997); the metastasis of tumor cells—ibid, Broadhurst, M. J., et al., European Patent Application 276,436 (published 1987), Reich, R., et al., *Cancer Res.*, Vol. 48, p. 3307–3312 (1988); multiple sclerosis—Gijbels et al., *J. Clin. Invest.*, vol. 94, p. 2177–2182 (1994); and various ulcerations or ulcerative conditions of tissue. For example, ulcerative conditions can result in the cornea as the result of alkali burns or as a result of infection by Pseudomonas aeruginosa, Acanthamoeba, Herpes simplex and vaccinia viruses. Other examples of conditions characterized by undesired metalloprotease activity include periodontal disease, epidermolysis bullosa, fever, inflammation and scleritis (e.g., DeCicco et al., World Patent Publication WO 95/29892 published Nov. 9, 1995).

In view of the involvement of such metalloproteases in a number of disease conditions, attempts have been made to prepare inhibitors to these enzymes. A number of such inhibitors are disclosed in the literature. Examples include U.S. Pat. No. 5,183,900, issued Feb. 2, 1993 to Galardy; U.S. Pat. No. 4,996,358, issued Feb. 26, 1991 to Handa, et al.; U.S. Pat. No. 4,771,038, issued Sep. 13, 1988 to Wolanin, et al.; U.S. Pat. No. 4,743,587, issued May 10, 1988 to Dickens, et al., European Patent Publication No. 575,844, published Dec. 29, 1993 by Broadhurst, et al.; International Patent Publication No. WO 93/09090, published May 13, 1993 by Isomura, et al.; World Patent Publication 92/17460, published Oct. 15, 1992 by Markwell et al.; and European Patent Publication No. 498,665, published Aug. 12, 1992 by Beckett, et al.

It would be advantageous to inhibit these metalloproteases in treating diseases related to unwanted metalloprotease activity. Though a variety of MP inhibitors have been prepared, there is a continuing need for potent matrix metalloprotease inhibitors useful in treating diseases associated with metalloprotease activity.

SUMMARY OF THE INVENTION

The invention provides compounds which are potent inhibitors of metalloproteases and which are effective in treating conditions characterized by excess activity of these enzymes. In particular, the present invention relates to compounds having a structure according to the following Formula (I):

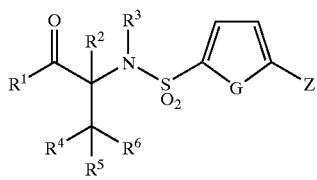

wherein:
(A) $R^1$ is selected from —OH and —NHOH;
(B) $R^2$ is selected from hydrogen, hydroxyl, alkoxy, alkyl, alkenyl, alkynyl, heteroalkyl, haloalkyl, cycloalkyl, heterocycloalkyl, aryl, arylalkyl, heteroaryl, heteroarylalkyl, and halogen;
(C) $R^3$ is selected from hydrogen, alkyl, alkenyl, alkynyl, heteroalkyl, haloalkyl, aryl, arylalkyl, heteroaryl, heteroarylalkyl, cycloalkyl, and heterocycloalkyl;
(D) $R^4$ is —$(CR^7R^{7'})_k$—X—$(CR^8R^{8'})_l$—E—A where:
  (1) k is from 0 to about 4;
  (2) l is from 0 to about 4;
  (3) each of $R^7$, $R^{7'}$, $R^8$, and $R^{8'}$, when present, is independently selected from hydrogen, alkyl, alkenyl, alkynyl, aryl, heteroalkyl, heteroaryl, cycloalkyl, heterocycloalkyl, halogen, and haloalkyl;
  (4) X is selected from —O—, —S—, —S(O)—, —S(O$_2$)—, —N(R$^9$)—, —N(COR$^9$)—, —N(CO$_2$R$^9$)—, —N(CONR$^9$R$^{9'}$)—, and —N(SO$_2$R$^9$)—, where (i) each $R^9$ and $R^{9'}$, when present, is independently selected from hydrogen, alkyl, alkenyl, alkynyl, heteroalkyl, haloalkyl, aryl, arylalkyl, heteroaryl, heteroarylalkyl, cycloalkyl, and heterocycloalkyl, or (ii) $R^9$ and $R^{9'}$, together with the nitrogen atom to which they are bonded, join to form an optionally substituted heterocyclic ring containing from 5 to 8 ring atoms of which from 1 to 3 are heteroatoms;
  (5) E is selected from a covalent bond, —O—, —S—, —S(O)—, —S(O$_2$)—, —N(R$^{10}$)—, —N(COR$^{10}$)—, —N(CO$_2$R$^{10}$)—, —N(CONR$^{10}$R$^{10'}$)—, and —N(SO$_2$R$^{10}$)—, where (i) each $R^{10}$ and $R^{10'}$, when present, is independently selected from hydrogen, alkyl, alkenyl, alkynyl, heteroalkyl, haloalkyl, aryl, arylalkyl, heteroaryl, heteroarylalkyl, cycloalkyl, and heterocycloalkyl, or (ii) $R^{10}$ and $R^{10'}$, together with the nitrogen atom to which they are bonded, join to form an optionally substituted heterocyclic ring containing from 5 to 8 ring atoms of which from 1 to 3 are heteroatoms; provided that when l=0, E is a covalent bond; and
  (6)
    (a) A is selected from hydrogen, alkyl, alkenyl, alkynyl, heteroalkyl, haloalkyl, aryl, arylalkyl, heteroaryl, heteroarylalkyl, cycloalkyl, and heterocycloalkyl; or
    (b) A, together with $R^7$, $R^{7'}$, $R^8$, $R^{8'}$, $R^9$, $R^{9'}$, $R^{10}$, or $R^{10'}$, join to form an optionally substituted heterocyclic ring containing from 5 to 8 ring atoms of which from 1 to 3 are heteroatoms;
(E) $R^5$ is selected from hydrogen, alkyl, alkenyl, alkynyl, heteroalkyl, haloalkyl, aryl, arylalkyl, heteroaryl, heteroarylalkyl, cycloalkyl, and heterocycloalkyl;
(F) $R^6$ is selected from alkyl, alkenyl, alkynyl, heteroalkyl, haloalkyl, aryl, arylalkyl, heteroaryl, heteroarylalkyl, cycloalkyl, heterocycloalkyl, and hydroxyl; provided that when k>0, $R^6$ is —OH and when k=0, $R^6$ is not —OH;
(G) G is selected from —S—, —O—, —N(R$^{11}$)—, —C(R$^{11}$)=C(R$^{11'}$)—, —N=C(R$^{11}$)—, and —N=N—, where each $R^{11}$ and $R^{11'}$, when present, is independently selected from hydrogen, alkyl, alkenyl, alkynyl, heteroalkyl, aryl, heteroaryl, cycloalkyl, and heterocycloalkyl;
(H) Z is selected from:
  (1) cycloalkyl and heterocycloalkyl;
  (2) —L—$(CR^{12}R^{12'})_a$—$R^{13}$ where:
    (a) a is from 0 to about 4;
    (b) L is selected from —C≡C—, —CH=CH—, —N=N—, —O—, —S— and —SO$_2$—;
    (c) each $R^{12}$ and $R^{12'}$, when present, is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and
    (d) $R^{13}$ is selected from hydrogen, aryl, heteroaryl, alkyl, alkenyl, alkynyl, heteroalkyl, haloalkyl, heterocycloalkyl and cycloalkyl; and, if L is —C≡C— or —CH=CH—, then $R^{13}$ may also be selected from —CON($R^{14}R^{14'}$) where (i) $R^{14}$ and $R^{14'}$ are independently selected from hydrogen, alkyl, alkenyl, alkynyl, haloalkyl, heteroalkyl, aryl, heteroaryl, cycloalkyl, and heterocycloalkyl, or (ii) $R^{14}$ and $R^{14'}$, together with the nitrogen atom to which they are bonded, join to form an optionally substituted heterocyclic ring containing from 5 to 8 ring atoms of which from 1 to 3 are heteroatoms;
  (3) —$NR^{15}R^{15'}$ where:
    (a) $R^{15}$ and $R^{15'}$ each is independently selected from hydrogen, alkyl, alkenyl, alkynyl, heteroalkyl, haloalkyl, aryl, heteroaryl, cycloalkyl, heteroalkyl and —C(O)—Q—$(CR^{16}R^{16'})_b$—$R^{17}$ where:
      (i) b is from 0 to about 4;
      (ii) Q is selected from a covalent bond and —N(R$^{18}$)—; and
      (iii) each $R^{16}$ and $R^{16'}$, when present, is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; each $R^{17}$ and $R^{18}$ is independently selected from hydrogen, alkyl, alkenyl, alkynyl, heteroalkyl, haloalkyl, aryl, heteroaryl, cycloalkyl, and heterocycloalkyl, or $R^{17}$ and $R^{18}$, together with the atoms to which they are bonded, join to form an optionally substituted heterocyclic ring containing from 5 to 8 ring atoms of which from 1 to 3 are heteroatoms; or $R^{15}$ and $R^{18}$, together with the nitrogen atoms to which they are bonded, join to form an optionally substituted heterocyclic ring containing from 5 to 8 ring atoms of which from 2 to 3 are heteroatoms; or
    (b) $R^{15}$ and $R^{15'}$, together with the nitrogen atom to which they are bonded, join to form an optionally substituted heterocyclic ring containing from 5 to 8 ring atoms of which from 1 to 3 are heteroatoms; and (4)

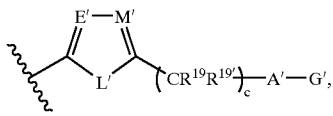

where:
(a) E' and M' are independently selected from —CH— and —N—;
(b) L' is selected from —S—, —O—, —N($R^{20}$)—, —C($R^{20}$)=C($R^{20'}$)—, N=C($R^{20}$)—, and —N=N—, where each $R^{20}$ and $R^{20'}$, when present, is independently selected from hydrogen, alkyl, alkenyl, alkynyl, heteroalkyl, aryl, heteroaryl, cycloalkyl, and heterocycloalkyl;
(c) c is from 0 to about 4;
(d) each $R^{19}$ and $R^{19'}$, when present, is independently selected from hydrogen, alkyl, alkenyl, alkynyl, aryl, heteroalkyl, heteroaryl, cycloalkyl, heterocycloalkyl, halogen, haloalkyl, hydroxy, and alkoxy;
(e) A' is selected from a covalent bond, —O—, —$SO_d$—, —C(O)—, C(O)N($R^{21}$)—, —N($R^{21}$)—, and —N($R^{21}$)C(O)—; where d is from 0 to 2 and $R^{21}$ is selected from hydrogen, alkyl, alkenyl, alkynyl, aryl, heteroaryl, heteroalkyl, heteroaryl, cycloalkyl, heterocycloalkyl, and haloalkyl; and
(f) G' is —($CR^{22}R^{22'}$)$_e$—$R^{23}$ where e is from 0 to about 4; each $R^{22}$ and $R^{22'}$, when present, is independently selected from hydrogen, alkyl, alkenyl, alkynyl, aryl, heteroalkyl, heteroaryl, cycloalkyl, heterocycloalkyl, halogen, haloalkyl, hydroxy, alkoxy and aryloxy; and $R^{23}$ is selected from hydrogen, alkyl, alkenyl, alkynyl, halogen, heteroalkyl, haloalkyl, aryl, heteroaryl, cycloalkyl, and heterocycloalkyl; or $R^{21}$ and $R^{23}$, together with the atoms to which they are bonded, join to form an optionally substituted heterocyclic ring containing from 5 to 8 atoms of which 1 to 3 are heteroatoms; or $R^{20}$ and $R^{23}$, together with the atoms to which they are bonded, join to form an optionally substituted heterocyclic ring containing from 5 to 8 atoms of which 1 to 3 are heteroatoms;

or an optical isomer, diastereomer or enantiomer for Formula (I), or a pharmaceutically-acceptable salt, or biohydrolyzable amide, ester, or imide thereof.

This invention also includes optical isomers, diastereomers and enantiomers of the formula above, and pharmaceutically-acceptable salts, biohydrolyzable amides, esters, and imides thereof.

The compounds of the present invention are useful for the treatment of diseases and conditions which are characterized by unwanted metalloprotease activity. Accordingly, the invention further provides pharmaceutical compositions comprising these compounds. The invention still further provides methods of treatment for metalloprotease-related maladies.

DETAILED DESCRIPTION OF THE INVENTION

I. Terms and Definitions

The following is a list of definitions for terms used herein.

"Acyl" or "carbonyl" is a radical formed by removal of the hydroxy from a carboxylic acid (i.e., R—C(=O)—). Preferred acyl groups include (for example) acetyl, formyl, and propionyl.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon-carbon double bond and having 2 to 15 carbon atoms, preferably 2 to 10, more preferably 2 to 4 carbon atoms. "Alkyne" is a hydrocarbon chain having at least one (preferably only one) carbon-carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

Also, as referred to herein, a "lower" alkyl, alkene or alkyne moiety (e.g., "lower alkyl") is a chain comprised of 1 to 6, preferably from 1 to 4, carbon atoms in the case of alkyl and 2 to 6, preferably 2 to 4, carbon atoms in the case of alkene and alkyne.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, napthyloxy, methoxyphenoxy, and methylenedioxyphenoxy.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, and cyclohexyl.

"Halo" or "halogen" is fluoro, chloro, bromo or iodo. Preferred halo are fluoro, chloro and bromo; more preferred typically are chloro and fluoro.

"Haloalkyl" is a straight, branched, or cyclic hydrocarbon substituted with one or more halo substituents. Preferred are $C_1$–$C_{12}$ haloalkyls; more preferred are $C_1$–$C_6$ haloalkyls; still more preferred still are $C_1$–$C_3$ haloalkyls. Preferred halo substituents are fluoro and chloro.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, heteroaryloxy, or any combination thereof. Preferred heteroaryl rings include, but are not limited to, the following:

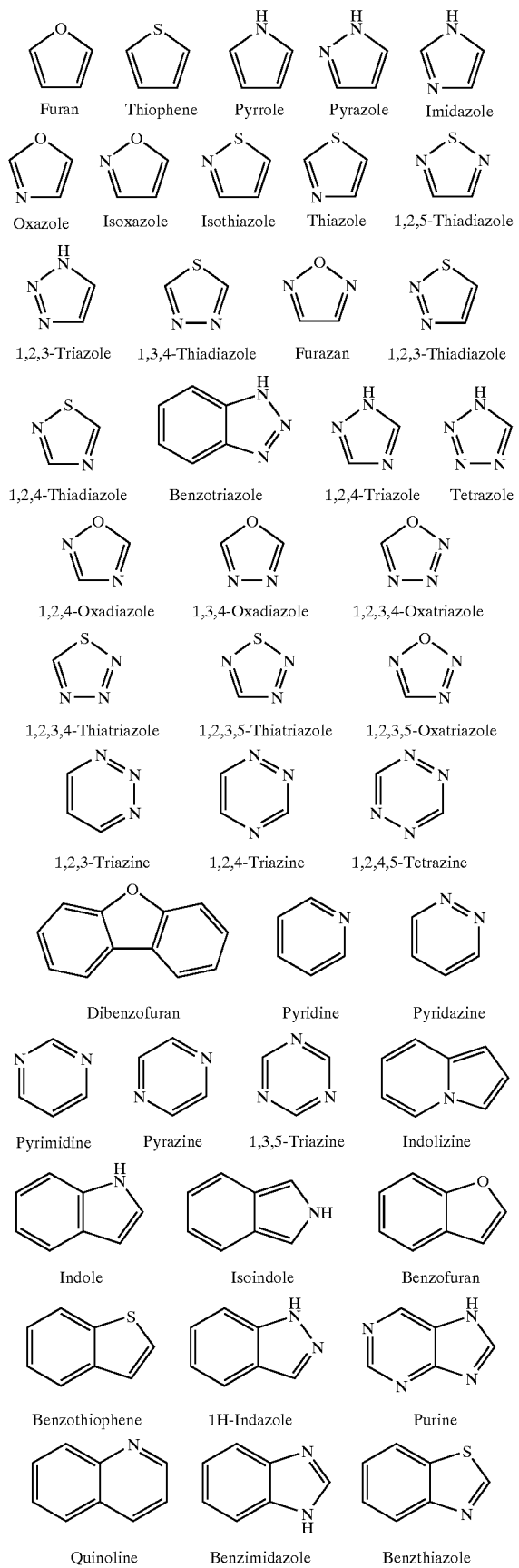

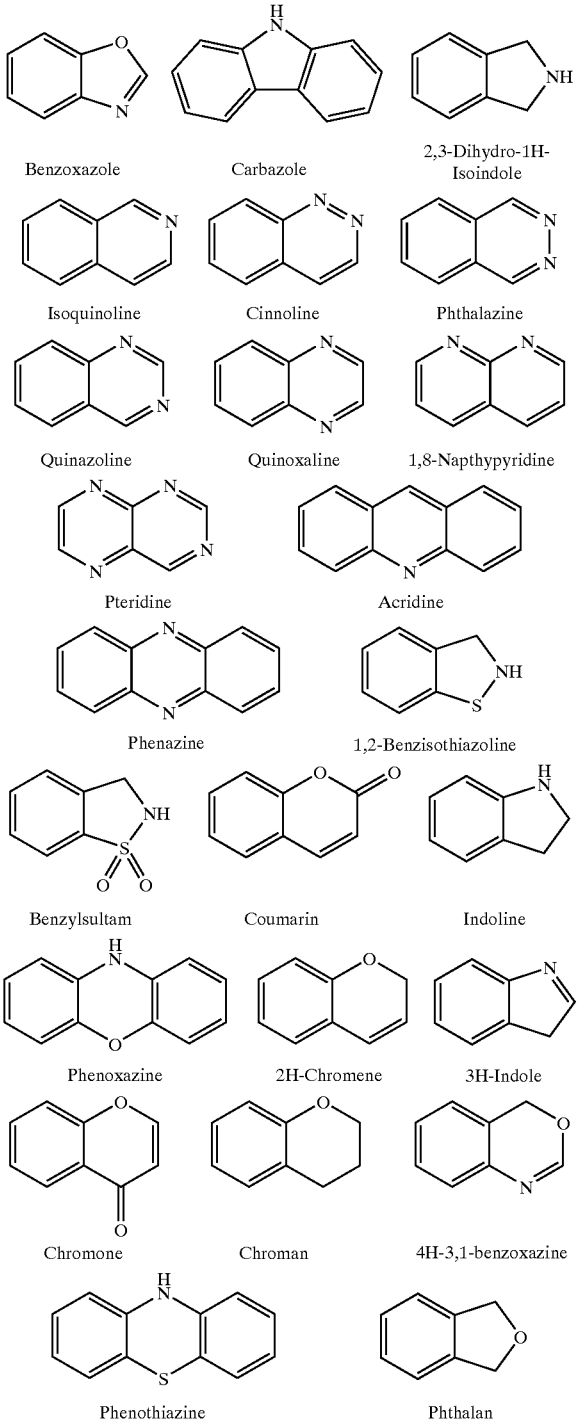

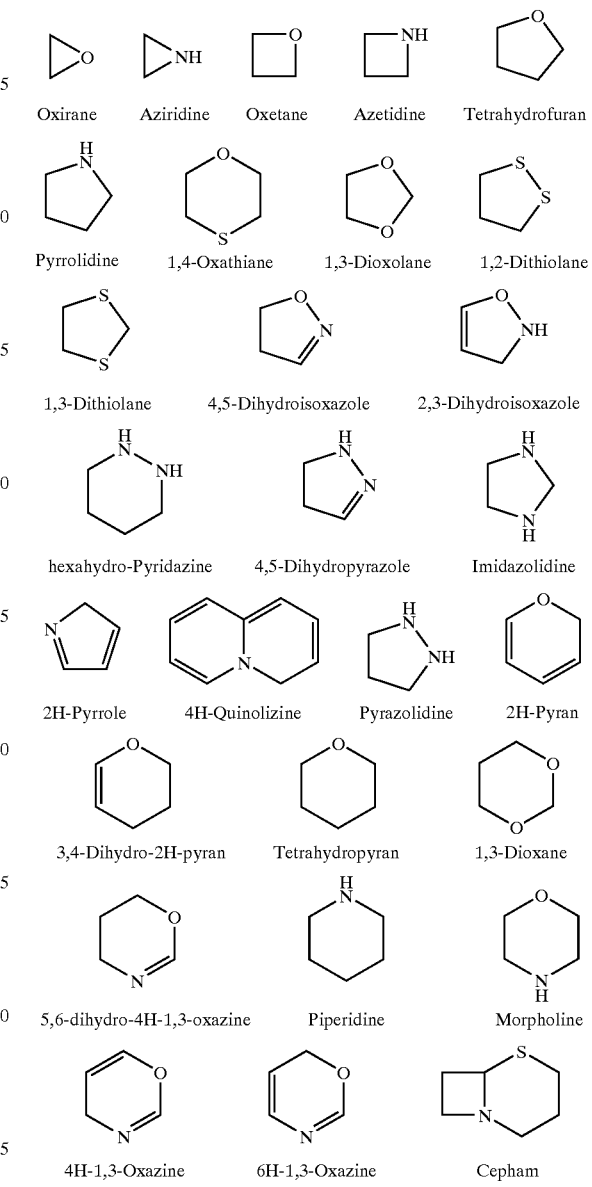

member atoms (carbon and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms. Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, aryloxy or any combination thereof. Preferred substituents on heterocycloalkyl include halo and haloalkyl. Preferred heterocycloalkyl rings include, but are not limited to, the following:

"Heteroaryloxy" is an oxygen radical having a heteroaryl substituent (i.e., —O-heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic, or are fused, bridged, or spiro bicyclic ring systems. Monocyclic heterocycloalkyl rings contain from about 3 to about 9

-continued

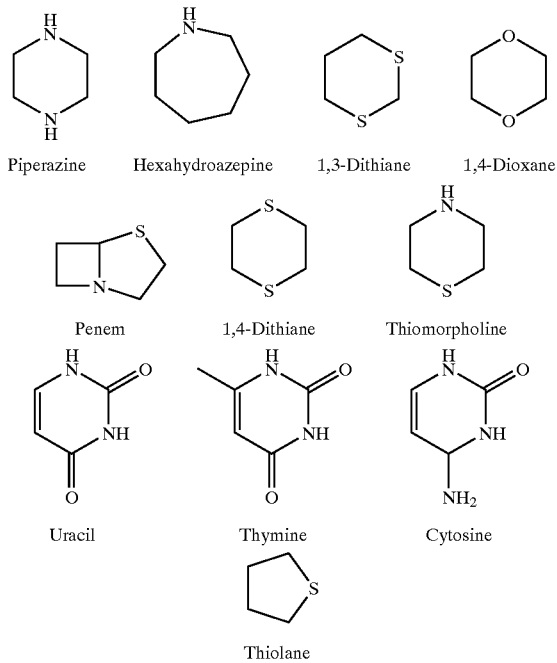

Piperazine   Hexahydroazepine   1,3-Dithiane   1,4-Dioxane

Penem   1,4-Dithiane   Thiomorpholine

Uracil   Thymine   Cytosine

Thiolane

As used herein, "mammalian metalloprotease" refers to the proteases disclosed in the "Background" section of this application. The compounds of the present invention are preferably active against "mammalian metalloproteases", including any metal-containing (preferably zinc-containing) enzyme found in animal, preferably mammalian, sources capable of catalyzing the breakdown of collagen, gelatin or proteoglycan under suitable assay conditions. Appropriate assay conditions can be found, for example, in U.S. Pat. No. 4,743,587, which references the procedure of Cawston, et al., *Anal. Biochem.* (1979) 99:340–345; use of a synthetic substrate is described by Weingarten, H., et al., *Biochem. Biophy. Res. Comm.* (1984) 139:1184–1187. See also Knight, C. G. et al., "A Novel Coumarin-Labelled Peptide for Sensitive Continuous Assays of the Matrix Metalloproteases", *FEBS Letters*, Vol. 296, pp. 263–266 (1992). Any standard method for analyzing the breakdown of these structural proteins can, of course, be used. The present compounds are more preferably active against metalloprotease enzymes that are zinc-containing proteases which are similar in structure to, for example, human stromelysin or skin fibroblast collagenase. The ability of candidate compounds to inhibit metalloprotease activity can, of course, be tested in the assays described above. Isolated metalloprotease enzymes can be used to confirm the inhibiting activity of the invention compounds, or crude extracts which contain the range of enzymes capable of tissue breakdown can be used.

"Spirocycle" is an alkyl or heteroalkyl diradical substituent of alkyl or heteroalkyl wherein said diradical substituent is attached geminally and wherein said diradical substituent forms a ring, said ring containing 4 to 8 member atoms (carbon or heteroatom), preferably 5 or 6 member atoms.

While alkyl, heteroalkyl, cycloalkyl, and heterocycloalkyl groups may be substituted with hydroxy, amino, and amido groups as stated above, the following are not envisioned in the invention:

1. Enols (OH attached to a carbon-carbon double bond).
2. Amino groups attached to a carbon-carbon double bond (except for vinylogous amides).
3. More than one hydroxy, amino, or amido attached to a single carbon (except where two nitrogen atoms are attached to a single carbon atom and all three atoms are member atoms within a heterocycloalkyl ring).
4. Hydroxy, amino, or amido attached to a carbon that also has a halogen attached to it.

A "pharmaceutically-acceptable salt" is a cationic salt formed at any acidic (e.g., hydroxamic or carboxylic acid) group, or an anionic salt formed at any basic (e.g., amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

A "biohydrolyzable amide" is an amide of a hydroxamic acid-containing (i.e., $R^1$ in Formula (I) is —NHOH) metalloprotease inhibitor that does not interfere with the inhibitory activity of the compound, or that is readily converted in vivo by an animal, preferably a mammal, more preferably a human subject, to yield an active metalloprotease inhibitor. Examples of such amide derivatives are alkoxyamides, where the hydroxyl hydrogen of the hydroxamic acid of Formula (I) is replaced by an alkyl moiety, and acyloxyamides, where the hydroxyl hydrogen is replaced by an acyl moiety (i.e., R—C(=O)—).

A "biohydrolyzable hydroxy imide" is an imide of a hydroxamic acid-containing metalloprotease inhibitor that does not interfere with the metalloprotease inhibitory activity of these compounds, or that is readily converted in vivo by an animal, preferably a mammal, more preferably a human subject to yield an active metalloprotease inhibitor. Examples of such imide derivatives are those where the amino hydrogen of the hydroxamic acid of Formula (I) is replaced by an acyl moiety (i.e., R—C(=O)—).

A "biohydrolyzable ester" is an ester of a carboxylic acid-containing (i.e., $R^1$ in Formula (I) is —OH) metalloprotease inhibitor that does not interfere with the metalloprotease inhibitory activity of these compounds or that is readily converted by an animal to yield an active metalloprotease inhibitor. Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkyl acylamino alkyl esters (such as acetamidomethyl esters).

A "solvate" is a complex formed by the combination of a solute (e.g., a metalloprotease inhibitor) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the metalloprotease inhibitor (e.g., water, ethanol, acetic acid, N,N-dimethylformamide and others known or readily determined by the skilled artisan).

The terms "optical isomer", "stereoisomer", and "diastereomer" have the standard art recognized meanings (see, e.g., *Hawley's Condensed Chemical Dictionary*, 11th Ed.). The illustration of specific protected forms and other derivatives of the compounds of the instant invention is not intended to be limiting. The application of other useful protecting groups, salt forms, etc. is within the ability of the skilled artisan.

II. Compounds

The subject invention involves compounds of Formula (I):

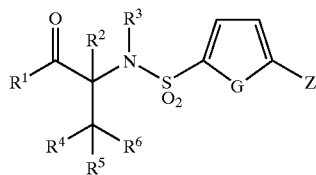

where $R^1$, $R^2$, $R^3$, $R^4$, $R^5$, $R^6$, G and Z have the meanings described above. The following provides a description of particularly preferred moieties, but is not intended to limit the scope of the claims.

$R^1$ is selected from —OH and —NHOH; preferably —OH.

$R^2$ is selected from hydrogen, hydroxyl, alkoxy, alkyl, alkenyl, alkynyl, heteroalkyl, haloalkyl, cycloalkyl, heterocycloalkyl, aryl, arylalkyl, heteroaryl, heteroarylalkyl, and halogen; preferably hydrogen or alkyl, more preferably hydrogen.

$R^3$ is selected from hydrogen, alkyl, alkenyl, alkynyl, heteroalkyl, haloalkyl, aryl, arylalkyl, heteroaryl, heteroarylalkyl, cycloalkyl, and heterocycloalkyl; preferably hydrogen or alkyl, more preferably hydrogen.

$R^4$ is —$(CR^7R^{7'})_k$—X—$(CR^8R^{8'})_l$—E—A. Each of k and l is independently selected from 0, 1, 2, 3 or 4; preferably k is 0, 1, 2 or 3; preferably l is 0, 1 or 2. Each of $R^7$, $R^{7'}$, $R^8$, and $R^{8'}$ is independently selected from hydrogen, alkyl, alkenyl, alkynyl, aryl, heteroalkyl, heteroaryl, cycloalkyl, heterocycloalkyl, halogen and haloalkyl; preferably all are hydrogen.

X is selected from —O—, —S—, —S(O)—, —S(O$_2$)—, —N($R^9$)—, —N(COR$^9$)—, —N(CO$_2$R$^9$)—, —N(CONR$^9$R$^{9'}$)—, and —N(SO$_2$R$^9$)—, where each $R^9$ and $R^{9'}$ is independently selected from hydrogen, alkyl, alkenyl, alkynyl, heteroalkyl, haloalkyl, aryl, arylalkyl, heteroaryl, heteroarylalkyl, cycloalkyl, and heterocycloalkyl (preferably each $R^9$ and $R^{9'}$ is hydrogen), or (ii) $R^9$ and $R^{9'}$ together with the nitrogen atom to which they are bonded, join to form an optionally substituted heterocyclic ring containing from 5 to 8 ring atoms of which from 1 to 3 are heteroatoms. Preferably X is —O—, —S—, —N(SO$_2$R$^9$), —N(COR$^9$), —NCO$_2$R$^9$), where $R^9$ is preferably lower alkyl or aryl.

E is selected from a covalent bond, —O—, —S—, —S(O), —S(O$_2$)—, —N($R^{10}$)—, —N(COR$^{10}$)—, —(CO$_2$R$^{10}$)—, —N(CONR$^{10}$R$^{10'}$)—, and —N(SO$_2$R$^{10}$)—, where (i) each $R^{10}$ and $R^{10'}$ is independently selected from hydrogen, alkyl, alkenyl, alkynyl, heteroalkyl, haloalkyl, aryl, arylalkyl, heteroaryl, heteroarylalkyl, cycloalkyl, and heterocycloalkyl (preferably each $R^{10}$ and $R^{10'}$ is hydrogen), or (ii) $R^{10}$ and $R^{10'}$ together with the nitrogen atom to which they are bonded, join to form an optionally substituted heterocyclic ring containing from 5 to 8 ring atoms of which from 1 to 3 are heteroatoms. Preferably, E is covalent bond, —O—, —S—, —N(SO$_2$R$^{10}$)—, —N(COR$^{10}$), or —N(CO$_2$R$^{10}$)—, where $R^{10}$ is preferably lower alkyl or aryl. When l=0, E is a covalent bond.

A is selected from hydrogen, alkyl, alkenyl, alkynyl, heteroalkyl, haloalkyl, aryl, arylalkyl, heteroaryl, heteroarylalkyl, cycloalkyl, and heterocycloalkyl; preferably A is alkyl, aryl, arylalkyl, heteroaryl or heteroarylalkyl.

$R^5$ is selected from hydrogen, alkyl, alkenyl, alkynyl, heteroalkyl, haloalkyl, aryl, arylalkyl, heteroaryl, heteroarylalkyl, cycloalkyl, and heterocycloalkyl; preferably hydrogen or lower alkyl; more preferably hydrogen.

$R^6$ is selected from alkyl, alkenyl, alkynyl, heteroalkyl, haloalkyl, aryl, arylalkyl, heteroaryl, heteroarylalkyl, cycloalkyl, heterocycloalkyl, and hydroxyl; preferably aryl, heteroaryl or hydroxyl. When k>0, $R^6$ is —OH and when k=0, $R^6$ is not —OH.

G is selected from —S—, —O—, —N($R^{11}$)—, —C($R^{11'}$)=C($R^{11'}$)—, —N=C($R^{11}$)—, and —N=N—; in a preferred embodiment, G is —S— or —C($R^{11}$)=C($R^{11'}$)—. Each $R^{11}$ and $R^{11'}$ is independently selected from hydrogen, alkyl, alkenyl, alkynyl, heteroalkyl, aryl, heteroaryl, cycloalkyl, and heterocycloalkyl; preferably at least one of $R^{11}$ and $R^{11'}$ is hydrogen, more preferably both are hydrogen.

Z is selected from cycloalkyl and heterocycloalkyl; —L—$(CR^{12}R^{12'})_a$—$R^{13}$; —$NR^{15}R^{15'}$;

and 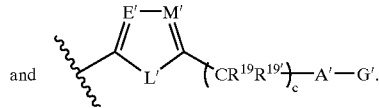

When Z is cycloalkyl or heterocycloalkyl, preferred is where Z is an optionally substituted piperidine or piperazine.

When Z is —L—$(CR^{12}R^{12'})_a$—$R^{13}$, a is 0, 1, 2, 3 or 4, preferably 0 or 1. L is selected from —C≡C—, —CH=CH—, —N=N—, —O—, —S— and —S(O$_2$)—; preferred is where L is —C≡C—, —CH=CH—, —N=N—, —O— or —S—; more preferred is where L is —C≡C—, —CH=CH—, or —N=N—. Each $R^{12}$ and $R^{12'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably each $R^{12}$ is hydrogen and each $R^{12'}$ is independently hydrogen or lower alkyl $R^{13}$ is selected from aryl, heteroaryl, alkyl, alkenyl, alkynyl, heteroalkyl, haloalkyl, heterocycloalkyl and cycloalkyl; preferably $R^{13}$ is aryl, heteroaryl, heterocycloalkyl or cycloalkyl. However, if L is —C≡C— or —CH=CH—, then $R^{13}$ may also be selected from —C(O)NR$^{14}$R$^{14'}$ where (i) $R^{14}$ and $R^{14'}$ are independently selected from hydrogen, alkyl, alkenyl, alkynyl, haloalkyl, heteroalkyl, aryl, heteroaryl, cycloalkyl, and heterocycloalkyl, or (ii) $R^{14}$ and $R^{14'}$, together with the nitrogen atom to which they are bonded, join to form an optionally substituted heterocyclic ring containing from 5 to 8 (preferably 5 or 6) ring atoms of which from 1 to 3 (preferably 1 or 2) are heteroatoms.

When Z is —NR$^{15}$R$^{15'}$, $R^{15}$ and $R^{15'}$ each is independently selected from hydrogen, alkyl, alkenyl, alkynyl, heteroalkyl, haloalkyl, aryl, heteroaryl, cycloalkyl, heteroalkyl, and —C(O)—Q—$(CR^{16}R^{16'})_b$—$R^{17}$; preferably $R^{15}$ and $R^{15'}$ are independently selected from hydrogen, alkyl, aryl and —C(O)—Q—$(CR^{16}R^{16'})_b$—$R^{17}$. When $R^{15}$ and/or $R^{15'}$ is —C(O)—Q—$(CR^{16}R^{16'})_b$—$R^{17}$, b is 0, 1, 2, 3 or 4; b is preferably 0 or 1. Q is selected from a covalent bond and —NR$^{18}$—; Q is preferably a covalent bond. Each $R^{16}$ and $R^{16'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably each $R^{16}$ is hydrogen and each $R^{16'}$ is independently hydrogen or lower alkyl. $R^{17}$ and $R^{18}$ each is independently selected from hydrogen, alkyl, alkenyl, alkynyl, heteroalkyl, haloalkyl, aryl, heteroaryl, cycloalkyl, and heterocycloalkyl (preferably one is aryl); or $R^{17}$ and $R^{18}$, together with the nitrogen atom to which they are bonded, join to form an optionally substituted heterocyclic ring containing from 5 to 8 (preferably 5 or 6) ring atoms of which from 1 to 3 (preferably 1 or 2) are heteroatoms; preferably $R^{17}$ is alkyl, aryl, heteroaryl, cycloalkyl or heterocycloalkyl. Alternatively, $R^{15}$ and $R^{18}$, together with the nitrogen atoms to which they are bonded, join to form an optionally substituted heterocyclic ring containing from 5 to 8 (preferably 5 or 6) ring atoms of which from 1 to 3 (preferably 1 or 2) are heteroatoms. Most preferred is where $R^{15}$ is hydrogen or lower alkyl and $R^{15'}$ is —C(O)—Q—$(CR^{16}R^{16'})_b$—$R^{17}$ where Q is a covalent bond, b=0, and $R^{17}$ is aryl.

Alternatively, $R^{15}$ and $R^{15'}$, together with the nitrogen atom to which they are bonded, join to form an optionally substituted heterocyclic ring containing from 5 to 8 (preferably 5 or 6) ring atoms of which from 1 to 3 (preferably 1 or 2) are heteroatoms.

When Z is

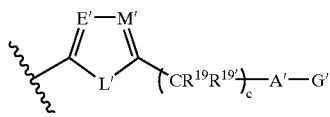

(referred to herein as Formula (A)), E' and M' are independently selected from —CH— and —N—; preferred is where E' is —CH and M' is —CH. L' is selected from —S—, —O—, —N($R^{20}$)—, —C($R^{20}$)=C($R^{20'}$)—, —N=C($R^{20}$)—, and —N=N—; preferably L is —C($R^{20}$)=C($R^{20'}$)—. $R^{20}$ and $R^{20'}$ each is independently selected from hydrogen, alkyl, alkenyl, alkynyl, heteroalkyl, aryl, heteroaryl, cycloalkyl, and heterocycloalkyl; preferably hydrogen or lower alkyl. c is 0, 1, 2, 3 or 4, preferably 0 or 1. Each $R^{19}$ and $R^{19'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably each $R^{19}$ is hydrogen and each $R^{19'}$ is independently hydrogen or lower alkyl. A' is selected from a covalent bond, —O—, —SO$_d$—, —C(O)—, —C(O)N($R^{21}$)—, —N($R^{21}$)—, and —N($R^{21}$)C(O)—; preferably A' is —O— or —S—. d is 0, 1 or 2. $R^{21}$ is selected from hydrogen, alkyl, alkenyl, alkynyl, aryl, heteroaryl, heteroalkyl, heteroaryl, cycloalkyl, heterocycloalkyl, and haloalkyl; $R^{21}$ is preferably lower alkyl or aryl. G' is —$(CR^{22}R^{22'})_e$—$R^{23}$. e is 0, 1, 2, 3 or 4, preferably 0 or 1. Each $R^{22}$ and $R^{22'}$ is independently selected from hydrogen, alkyl, alkenyl, alkynyl, aryl, heteroalkyl, heteroaryl, cycloalkyl, heterocycloalkyl, halogen, haloalkyl, hydroxy, alkoxy and aryloxy; preferably each $R^{22}$ is hydrogen and each $R^{22'}$ is independently hydrogen or lower alkyl. $R^{23}$ is selected from hydrogen, alkyl, alkenyl, alkynyl, aryl, halogen, heteroalkyl, haloalkyl, aryl, heteroaryl, cycloalkyl, and heterocycloalkyl; preferably $R^{23}$ is lower alkyl or aryl. Alternatively, $R^{21}$ and $R^{23}$, together with the atoms to which they are bonded, join to form an optionally substituted heterocyclic ring containing from 5 to 8 (preferably 5 or 6) atoms of which 1 to 3 (preferably 1 or 2) are heteroatoms. Alternatively, $R^{20}$ and $R^{23}$, together with the atoms to which they are bonded, join to form an optionally substituted heterocyclic ring containing from 5 to 8 (preferably 5 or 6) atoms of which 1 to 3 (preferably 1 or 2) are heteroatoms.

Most preferred compounds are those where Z is —$NR^{15}R^{15'}$ or

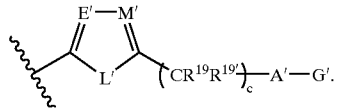

Preferred sub-genuses of compounds are those carboxylic acid-containing compounds having a structure according to the following Formula (II) or Formula (III)

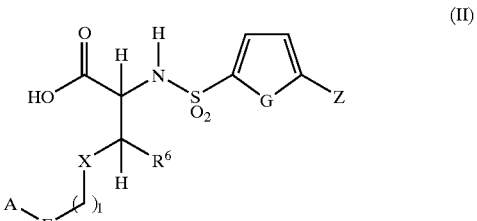

(II)

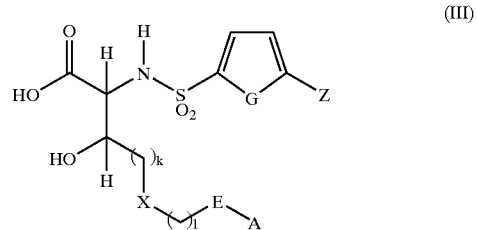

(III)

where $R^6$, X, k, l, E, A, G, and Z are as described with respect to Formula (I).

III. Compound Preparation

The compounds of the invention can be prepared using a variety of procedures. The starting materials used in preparing the compounds of the invention are known, made by known methods, or are commercially available. Particularly preferred syntheses are described in the following general reaction schemes. (The R groups used to illustrate the reaction schemes do not necessarily correlate to the respective R groups used to describe the various aspects of the Formula I compounds. That is, for example, $R^1$ in Formula (I) does not represent the same moiety as $R_1$ here). Specific examples for making the compounds of the present invention are set forth in Section VIII, below.

Scheme 1

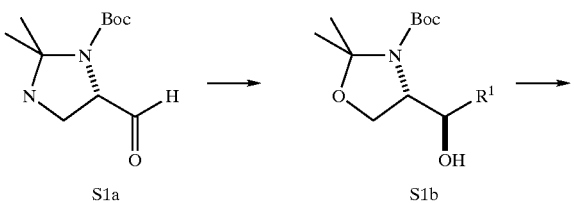

-continued

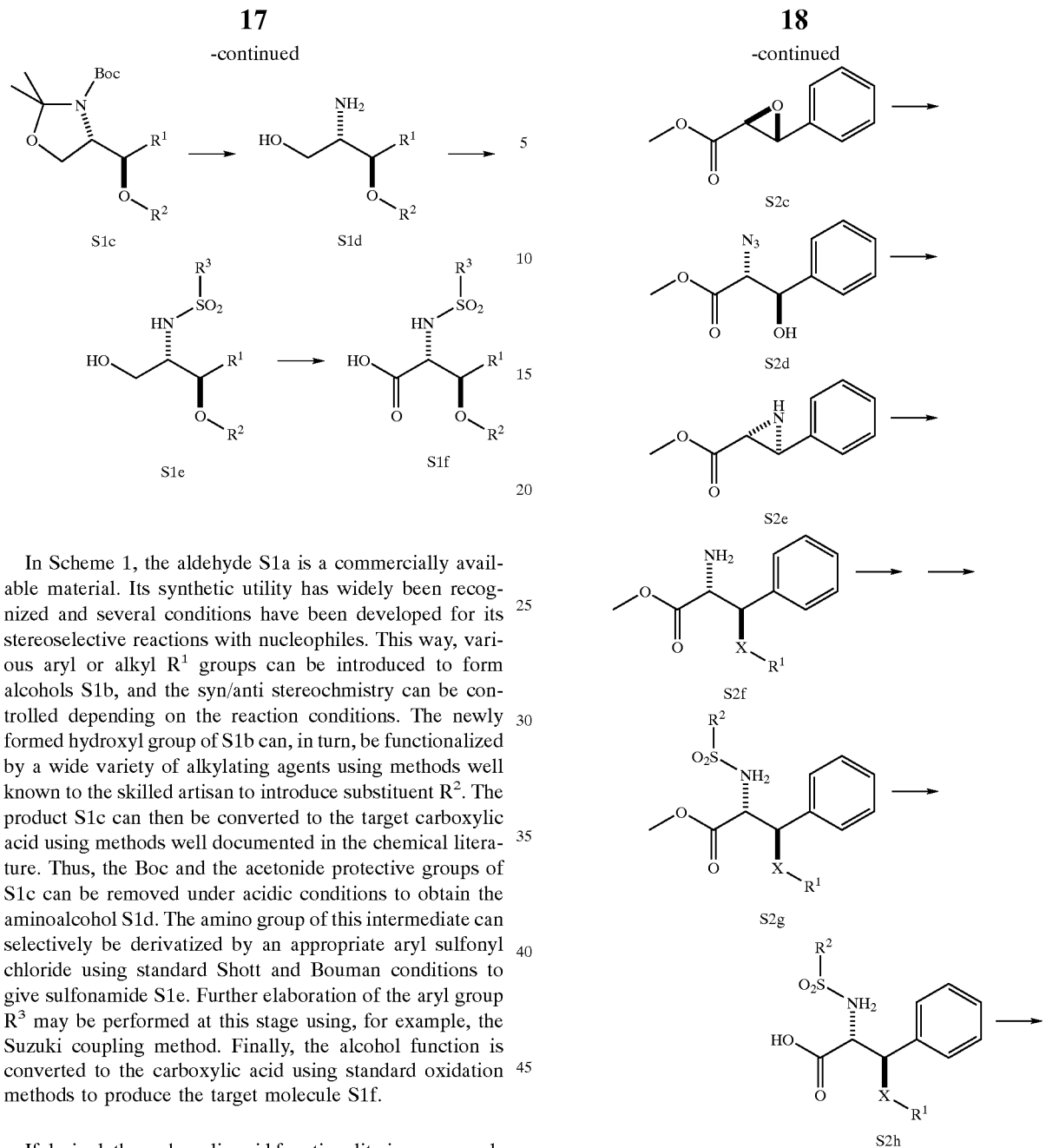

In Scheme 1, the aldehyde S1a is a commercially available material. Its synthetic utility has widely been recognized and several conditions have been developed for its stereoselective reactions with nucleophiles. This way, various aryl or alkyl $R^1$ groups can be introduced to form alcohols S1b, and the syn/anti stereochmistry can be controlled depending on the reaction conditions. The newly formed hydroxyl group of S1b can, in turn, be functionalized by a wide variety of alkylating agents using methods well known to the skilled artisan to introduce substituent $R^2$. The product S1c can then be converted to the target carboxylic acid using methods well documented in the chemical literature. Thus, the Boc and the acetonide protective groups of S1c can be removed under acidic conditions to obtain the aminoalcohol S1d. The amino group of this intermediate can selectively be derivatized by an appropriate aryl sulfonyl chloride using standard Shott and Bouman conditions to give sulfonamide S1e. Further elaboration of the aryl group $R^3$ may be performed at this stage using, for example, the Suzuki coupling method. Finally, the alcohol function is converted to the carboxylic acid using standard oxidation methods to produce the target molecule S1f.

If desired, the carboxylic acid functionality in compounds of type S1f can be converted to the hydroxamic acid by coupling with hydroxylamine using a mixed anhydride method or by forming of an intermediate acid chloride.

Scheme 2

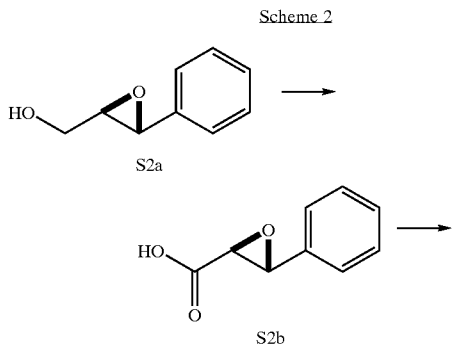

In Scheme 2, the commercially available epoxy-alcohol S2a is converted to the aziridine ester S2e using known methodology (Zwanenburg et. al., *Rec. Trav. Chim. Pay. Bas* 1992, 111, 1). First, the alcohol is oxidized and the resulting carboxylic acids S2b is esterified to give the epoxyester S2c. The epoxide ring of S2c can then be opened in the reaction with sodium azide in the presence of ammonium chloride to give the azido-alcohol S2d as a mixture of regioisomers. The aziridine S2e, which can be obtained from S2d upon treatment with triphenylphosphine, has been shown in chemical literature to be a highly versatile electrophile capable of undergoing ring opening reactions with various sulfur-, oxygen- and nitrogen-based nucleophiles. For example, thiols react with S2e under the catalysis of boron trifluoride etherate to give functionalized amino-acid S2f (X=S) in very good yields. Similariy, oxygen or nitrogen functionalized amino-acids S2f (X=O or N) can be prepared through acetic acid or azide addition, respectively (Legtersen, J. et. al., Rec. Trav. Chim. Pay. Bas 1992, 111, 59). The free amino group can then be derivatized with various sulfonyl chlorides to give sulfonamide esters S2g. If necessary, a more complex aryl sulfonyl group can be introduced in a sequence of several synthetic steps. Finally, the ester function is converted to the carboxylic acid using one of the standard hydrolysis methods to produce the target molecule S2h.

If desired, the ester functionality in compounds of type S2g can be converted to the hydroxamic acid by reaction with hydroxylamine under alkaline conditions.

Scheme 3

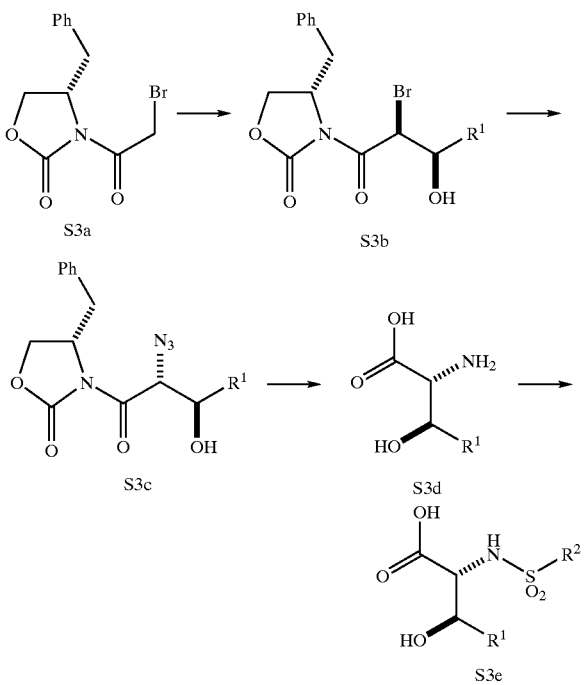

In Scheme 3, well known Evans chemistry is utilized to establish absolute and relative stereochemistry of chiral centers of the target aminoalcohol S3d. Thus, the oxazolidinone bromoacetate S3a is reacted with a selected aldehyde to obtain a bromoalcohol S3b with very high stereoselectivity. In the following step, standard conditions of $S_N2$ substitution are applied and the bromide atom is replaced by azide to give an intermediate S3c. Hydrolysis of the oxazolidinone group can be performed utilizing conditions well described in the chemical literature to produce a key intermediate aminoacid S3d. The free amino group of S3d can then be derivatized with various sulfonyl chlorides to give the target inhibitors S3e. If necessary, a more complex aryl sulfonyl groups can be introduced in a sequence of several synthetic steps. If desired, the carboxylic acid functionality in compounds of type S3e can be converted to the hydroxamic acid by coupling with hydroxylamine using a mixed anhydride method or by forming of an intermediate acid chloride.

These steps may be varied to increase yield of desired product. The skilled artisan will recognize the judicious choice of reactants, solvents, and temperatures is an important component in any successful synthesis. Determination of optimal conditions, etc. is routine. Thus, the skilled artisan can make a variety of compounds using the guidance of the schemes above.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, Advanced Organic Chemistry (Wiley), Carey and Sundberg, Advanced Organic Chemistry (Vol. 2) and other art that the skilled artisan is aware of.

The skilled artisan will also readily appreciate that certain reactions are best carried out when another potentially reactive functionality on the molecule is masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, Protecting Groups in Organic Synthesis. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

IV. Methods of Use

Metalloproteases (MPs) found in the body operate, in part, by breaking down the extracellular matrix, which comprises extracellular proteins and glycoproteins. Inhibitors of metalloproteases are useful in treating diseases caused, at least in part, by the breakdown of such proteins and glycoproteins. These proteins and glycoproteins play an important role in maintaining the size, shape, structure and stability of tissue in the body. Thus, MPs are intimately involved in tissue remodeling.

As a result of this activity, MPs have been said to be active in many disorders involving either the: (1) breakdown of tissues including opthalmic diseases; degenerative diseases, such as arthritis, multiple sclerosis and the like; and metastasis or mobility of tissues in the body; or (2) remodeling of tissues including cardiac disease, fibrotic disease, scarring, benign hyperplasia, and the like.

The compounds of the present invention prevent or treat disorders, diseases and/or unwanted conditions that are characterized by unwanted or elevated activity by MPs. For example, the compounds can be used to inhibit MPs which:

1. destroy structural proteins (i.e. the proteins that maintain tissue stability and structure);
2. interfere in inter/intracellular signaling, including those implicated in cytokine up-regulation, and/or cytokine processing and/or inflammation, tissue degradation and other maladies [Mohler K M, et al, Nature 370 (1994) 218–220, Gearing A J H, et al, Nature 370 (1994) 555–557 McGeehan G M, et al, Nature 370(1994) 558–561]; and
3. facilitate processes which are undesired in the subject being treated, for example, the processes of sperm maturation, egg fertilization and the like.

As used herein, an "MP related disorder" or "MP related disease" is one that involves unwanted or elevated MP activity in the biological manifestation of the disease or disorder; in the biological cascade leading to the disorder; or as a symptom of the disorder. This "involvement" of the MP includes:

1. The unwanted or elevated MP activity as a "cause" of the disorder or biological manifestation, whether the activity is elevated genetically, by infection, by autoimmunity, trauma, biomechanical causes, lifestyle [e.g. obesity] or by some other cause;
2. The MP as part of the observable manifestation of the disease or disorder. That is, the disease or disorder is measurable in terms of the increased MP activity. From a clinical standpoint, unwanted or elevated MP levels indicate the disease; however, MPs need not be the "hallmark" of the disease or disorder; or
3. The unwanted or elevated MP activity is part of the biochemical or cellular cascade that results or relates to the disease or disorder. In this respect, inhibition of the MP activity interrupts the cascade, and thus controls the disease.

The term "treatment" is used herein to mean that, at a minimum, administration of a compound of the present invention mitigates a disease associated with unwanted or eleveated MP activity in a mammalian subject, preferably in humans. Thus, the term "treatment" includes: preventing an MP-mediated disease from occurring in a mammal, particularly when the mammal is predisposed to acquiring the disease, but has not yet been diagnosed with the disease; inhibiting the MP-mediated disease; and/or alleviating the MP-mediated disease. Insofar as the methods of the present invention are directed to preventing disease states associated with unwanted MP activity, it is understood that the term "prevent" does not require that the disease state be completely thwarted. (See Webster's Ninth Collegiate Dictionary.) Rather, as used herein, the term preventing refers to the ability of the skilled artisan to identify a population that is susceptible to MP-related disorders, such that administration of the compounds of the present invention may occur prior to onset of the disease. The term does not imply that the disease state be completely avoided. For example, osteoarthritis (OA) is the most common rhueumatological disease with some joint changes radiologically detectable in 80% of people over 55 years of age. Fife, R. S., "A Short History of Osteoarthritis", Osteoarthritis: Diagnosis and Medical/Surgical Management, R. W. Moskowitz, D. S. Howell, V. M. Goldberg and H. J. Mankin Eds., p 11–14 (1992). A common risk factor that increases the incidence of OA is traumatic injury of the joint. Surgical removal of the meniscus following knee injury increases the risk of radiographically detectable OA and this risk increases with time. Roos, H et al. "Knee Osteoarthritis After Menisectomy: Prevalence of Radiographic Changes After Twenty-one Years, Compared with Matched Controls." Arthritis Rheum., Vol. 41, pp 687–693; Roos, H et al. "Osteoarthritis of the Knee After Injury to the Anterior Cruciate Ligament or Meniscus: The Influence of Time and Age." Osteoarthritis Cartilege., Vol. 3, pp 261–267 (1995). Thus, this patient population is identifiable and could receive administration of a compound of the present invention before progression of the disease. Thus, progression of OA in such individuals would be "prevented".

Advantageously, many MPs are not distributed evenly throughout the body. Thus, the distribution of MPs expressed in various tissues are often specific to those tissues. For example, the distribution of metalloproteases implicated in the breakdown of tissues in the joints is not the same as the distribution of metalloproteases found in other tissues. Though not essential for activity or efficacy, certain diseases, disorders, and unwanted conditions preferably are treated with compounds that act on specific MPs found in the affected tissues or regions of the body. For example, a compound which displays a higher degree of affinity and inhibition for an MP found in the joints (e.g. chondrocytes) would be preferred for treatment of a disease, disorder, or unwanted condition found there than other compounds which are less specific.

In addition, certain inhibitors are more bioavailable to certain tissues than others. Choosing an MP inhibitor which is more bioavailable to a certain tissue and which acts on the specific MPs found in that tissue, provides for specific treatment of the disease, disorder, or unwanted condition. For example, compounds of this invention vary in their ability to penetrate into the central nervous system. Thus, compounds may be selected to produce effects mediated through MPs found specifically outside the central nervous system.

Determination of the specificity of an inhibitor of a specific MP is within the skill of the artisan in that field. Appropriate assay conditions can be found in the literature. Specifically, assays are known for stromelysin and collagenase. For example, U.S. Pat. No. 4,743,587 references the procedure of Cawston, et al., *Anal Biochem* (1979) 99:340–345. See also, Knight, C. G. et al., "A Novel Coumarin-Labelled Peptide for Sensitive Continuous Assays of the Matrix Metalloproteases", *FEBS Letters*, Vol. 296, pp. 263–266 (1992). The use of a synthetic substrate in an assay is described by Weingarten, H., et al., *Biochem Biophy Res Comm* (1984) 139:1184–1187. Any standard method for analyzing the breakdown of structural proteins by MPs can, of course, be used. The ability of compounds of the invention to inhibit metalloprotease activity can be tested in the assays found in the literature, or variations thereof. Isolated metalloprotease enzymes can be used to confirm the inhibiting activity of the invention compounds, or crude extracts which contain the range of enzymes capable of tissue breakdown can be used.

The compounds of this invention are also useful for prophylactic or acute treatment. They are administered in any way the skilled artisan in the fields of medicine or pharmacology would desire. It is immediately apparent to the skilled artisan that preferred routes of administration will depend upon the disease state being treated and the dosage form chosen. Preferred routes for systemic administration include administration perorally or parenterally.

However, the skilled artisan will readily appreciate the advantage of administering the MP inhibitor directly to the affected area for many diseases, disorders, or unwanted conditions. For example, it may be advantageous to administer MP inhibitors directly to the area of the disease, disorder, or unwanted condition such as in the area affected by surgical trauma (e. g., angioplasty), scarring, burning (e.g., topical to the skin), or for opthalmic and periodontal indications.

Because the remodeling of bone involves MPs, the compounds of the invention are useful in preventing prosthesis loosening. It is known in the art that over time prostheses loosen, become painful, and may result in further bone injury, thus demanding replacement. The need for replacement of such prostheses includes those such as in joint replacements (for example hip, knee and shoulder replacements), dental prosthesis, including dentures, bridges and prosthesis secured to the maxilla and/or mandible.

MPs are also active in remodeling of the cardiovascular system (for example, in congestive heart failure). It has been suggested that one of the reasons angioplasty has a higher than expected long term failure rate (reclosure over time) is that MP activity is not desired or is elevated in response to what may be recognized by the body as "injury" to the basement membrane of the vessel. Thus regulation of MP activity in indications such as dilated cardiomyopathy, congestive heart failure, atherosclerosis, plaque rupture, reperfusion injury, ischemia, chronic obstructive pulmonary disease, angioplasty restenosis and aortic aneurysm may increase long term success of any other treatment, or may be a treatment in itself.

In skin care, MPs are implicated in the remodeling or "turnover" of skin. As a result, the regulation of MPs improves treatment of skin conditions including but not limited to, wrinkle repair, regulation and prevention and repair of ultraviolet induced skin damage. Such a treatment includes prophylactic treatment or treatment before the physiological manifestations are obvious. For example, the MP may be applied as a pre-exposure treatment to prevent ultaviolet damage and/or during or after exposure to prevent or minimize post-exposure damage. In, addition, MPs are implicated in skin disorders and diseases related to abnormal tissues that result from abnormal turnover, which includes metalloprotease activity, such as epidermolysis bullosa, psoriasis, scleroderma and atopic dermatitis. The compounds of the invention are also useful for treating the consequences of "normal" injury to the skin including scarring or "contraction" of tissue, for example, following burns. MP inhibition is also useful in surgical procedures involving the skin for prevention of scarring, and promotion of normal tissue growth including in such applications as limb reattachment and refractory surgery (whether by laser or incision).

In addition, MPs are related to disorders involving irregular remodeling of other tissues, such as bone, for example, in otosclerosis and/or osteoporosis, or for specific organs, such as in liver cirrhosis and fibrotic lung disease. Similarly, in diseases such as multiple sclerosis, MPs may be involved in the irregular modeling of blood brain barrier and/or myelin sheaths of nervous tissue. Thus, regulating MP activity may be used as a strategy in treating, preventing, and controlling such diseases.

MPs are also thought to be involved in many infections, including cytomegalovirus (CMV); retinitis; HIV, and the resulting syndrome, AIDS.

MPs may also be involved in extra vascularization where surrounding tissue needs to be broken down to allow new blood vessels such as in angiofibroma and hemangioma.

Since MPs break down the extracellular matrix, it is contemplated that inhibitors of these enzymes can be used as birth control agents, for example in preventing ovulation, in preventing penetration of the sperm into and through the extracellular milieu of the ovum, implantation of the fertilized ovum and in preventing sperm maturation.

Additionally, they are also contemplated to be useful in preventing or stopping premature labor and delivery.

Since MPs are implicated in the inflammatory response and in the processing of cytokines, the compounds are also useful as anti-inflammatories, for use in disease where inflammation is prevalent including, inflammatory bowel disease, Crohn's disease, ulcerative colitis, pancreatitis, diverticulitis, asthma or related lung disease, rheumatoid arthritis, gout and Reiter's Syndrome.

Where autoimmunity is the cause of the disorder, the immune response often triggers MP and cytokine activity. Regulation of MPs in treating such autoimmune disorders is a useful treatment strategy. Thus MP inhibitors can be used for treating disorders including, lupus erythmatosis, ankylosing spondylitis, and autoimmune keratitis. Sometimes the side effects of autoimmune therapy result in exacerbation of other conditions mediated by MPs, here MP inhibitor therapy is effective as well, for example, in autoimmune-therapy-induced fibrosis.

In addition, other fibrotic diseases lend themselves to this type of therapy, including pulmonary disease, bronchitis, emphysema, cystic fibrosis, acute respiratory distress syndrome (especially the acute phase response).

Where MPs are implicated in the undesired breakdown of tissue by exogenous agents, these can be treated with MP inhibitors. For example, they are effective as rattle snake bite antidote, as anti-vessicants, in treating allergic inflammation, septicemia and shock. In addition, they are useful as antiparasitics (e.g., in malaria) and antiinfectives. For example, they are thought to be useful in treating or preventing viral infection, including infection which would result in herpes, "cold" (e.g., rhinoviral infection), meningitis, hepatitis, HIV infection and AIDS.

MP inhibitors are also thought to be useful in treating Alzheimer's disease, amyotrophic lateral sclerosis (ALS), muscular dystrophy, complications resulting from or arising out of diabetes, especially those involving loss of tissue viability, coagulation, Graft vs. Host disease, leukemia, cachexia, anorexia, proteinuria, and regulation of hair growth.

For some diseases, conditions or disorders MP inhibition is contemplated to be a preferred method of treatment. Such diseases, conditions or disorders include, arthritis (including osteoarthritis and rheumatoid arthritis), cancer (especially the prevention or arrest of tumor growth and metastasis), ocular disorders (especially corneal ulceration, lack of corneal healing, macular degeneration, and pterygium), and gum disease (especially periodontal disease, and gingivitis)

Compounds preferred for, but not limited to, the treatment of arthritis (including osteoarthritis and rheumatoid arthritis) are those compounds that are selective for the matrix metalloproteases and the disintegrin metalloproteases. Compounds preferred for, but not limited to, the treatment of cancer (especially the prevention or arrest of tumor growth and metastasis) are those compounds that preferentially inhibit gelatinases or type IV collagenases. Compounds preferred for, but not limited to, the treatment of ocular disorders (especially corneal ulceration, lack of corneal healing, macular degeneration, and pterygium) are those compounds that broadly inhibit metalloproteases. Preferably these compounds are administered topically, more preferably as a drop or gel. Compounds preferred for, but not limited to, the treatment of gum disease (especially periodontal disease, and gingivitis) are those compounds that preferentially inhibit collagenases.

V. Compositions

The compositions of the invention comprise:
(a) a safe and effective amount of a compound of the invention; and
(b) a pharmaceutically-acceptable carrier.

As discussed above, numerous diseases are known to be mediated by excess or undesired metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences*, Mack Publishing Company, Easton, Pa., latest edition.

A "safe and effective amount" of a Formula (I) compound is an amount that is effective, to inhibit metalloproteases at the site(s) of activity in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the subject being treated. The choice of a pharmaceutically-acceptable carrier to be used in conjunction with the subject compound is determined in-part by the way the compound is to be administered.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents; stabilizers; antioxidants; preservatives; pyrogen-free water; isotonic saline; and phosphate buffer solutions.

Pharmaceutically-acceptable carriers for systemic adminisitration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition. If the subject compound is to be injected, the preferred pharmaceutically-acceptable carrier is sterile, physiological saline, with a blood-compatible suspending agent, the pH of which has preferably been adjusted to about 7.4.

The compositions of this invention are preferably provided in unit dosage form. As used herein, a "unit dosage form" is a composition of this invention containing an amount of a Formula (I) compound that is suitable for administration to an animal, preferably a mammal, more preferably a human subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and/or melting agents. Liquid oral dosage forms include aqueous solutions, emulsions, suspensions, solutions and/or suspensions reconstituted from non-effervescent granules, and effervescent preparations reconstituted from effervescent granules. Such liquid dose forms will optionally contain suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents such as calcium carbonate, sodium carbonate, mannitol, lactose and cellulose; binders such as starch, gelatin and sucrose; disintegrants such as starch, alginic acid and croscarmelose; and lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions may also contain one or more components such as the sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit® coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emollients, emulsifiers, thickening agents, solvents and the like.

VI. Methods of Administration

This invention also provides methods of treating disorders associated with excess or undesired metalloprotease activity in a human or other animal subject, by administering a safe and effective amount of a Formula (I) compound to said subject. As used herein, a "disorder associated with excess or undesired metalloprotease activity" is any disorder characterized by degradation of matrix proteins. The methods of the invention are useful in treating disorders described above.

As indicated, compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of compound to be administered, as well as the duration of treatment and whether the treatment is topical or systemic, are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of administration for treatment of rheumatoid arthritis is oral or parenteral dosing via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The compounds of the invention can be targeted to specific locations where the metalloprotease is accumulated by using targeting ligands. For example, to direct the compounds to metalloproteases contained in a tumor, the compound is conjugated to an antibody or fragment thereof which is immunoreactive with a tumor marker, as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carriers. The conjugates are formulated and administered as described below.

For localized conditions, topical administration is preferred. For example, to treat ulcerated cornea, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of skin inflammation, the compound is applied locally and topically in a gel, paste, salve or ointment. For treatment of oral diseases, the compound may be applied locally in a gel, paste, mouth wash, or implant. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases. Some bacterial metalloproteases may be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

VII. Preparation and Use of Antibodies

Metalloproteases active at a particularly undesired location (e.g., an organ or certain types of cells) can be targeted by conjugating the compounds of the invention to a targeting ligand specific for a marker at that location such as an antibody or fragment thereof or a receptor ligand. Conjugation methods are known in the art.

The invention is also directed to various other processes which take advantage of the unique properties of these compounds. Thus, in another aspect, the invention is directed to the compounds of Formula (I) conjugated to solid supports. These conjugates can be used as affinity reagents for the purification of a desired metalloprotease.

In another aspect, the invention is directed to the compounds of Formula (I) conjugated to label. As the compounds of the invention bind to at least one metalloprotease, the label can be used to detect the presence of relatively high levels of metalloprotease in vivo or in vitro cell culture.

In addition, the compounds of Formula (I) can be conjugated to carriers which permit the use of these compounds in immunization protocols to prepare antibodies specifically immunoreactive with the compounds of the invention. Typical conjugation methods are known in the art. These antibodies are then useful both in therapy and in monitoring the dosage of the inhibitors.

The invention compounds can also be coupled to labels such as scintigraphic labels, e.g., technetium 99 or 1–131, using standard coupling methods. The labeled compounds are administered to subjects to determine the locations of excess amounts of one or more metalloproteases in vivo. The ability of the inhibitors to selectively bind metalloprotease is thus taken advantage of to map the distribution of these enzymes in situ. The techniques can also be employed in histological procedures and the labeled invention compounds can be used in competitive immunoassays.

The following non-limiting examples of Sections VIII and IX illustrate the compounds, compositions, and methods of the present invention.

VIII. EXAMPLES

Compound Preparation

Typically tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merk) as appropriate. Thin layer chromatography analysis (TLC) is performed on glass mounted silica gel plates (200–300 mesh; Baker) and visualized with UV or 5% phosphomolybdic acid in ethanol (EtOH).

The following abbreviations are used herein:

| | |
|---|---|
| MeOH: methanol | $Et_3N$: triethylamine |
| EtOAc: ethylacetate | $Et_2O$: diethylether |
| Ph: phenyl | boc: t-butyloxycarbonyl |
| DMF: N,N-dimethylformamide | acac: acetyl acetate |
| DME: dimethoxyethane | dil.: dilute |
| conc.: concentrated | wrt.: with respect to |
| DCC: 1,3-Dicyclohexylcarbodiimide | HOBT: 1-Hydroxybenzotriazole |

The R groups used to illustrate the compound examples do not correlate to the respective R groups used to describe the various moieties of Formula (I). That is, for example, $R^1R^2$ and $R^3$ used to describe Formula (I) in the Summary of the Invention section and Section II of the Detailed Description do not represent the same moieties as $R_1$, $R_2$, and $R_3$ in this Section VIII.

Examples 1–3

The following chart shows the structure of compounds made according to the description in Examples 1–3 described below:

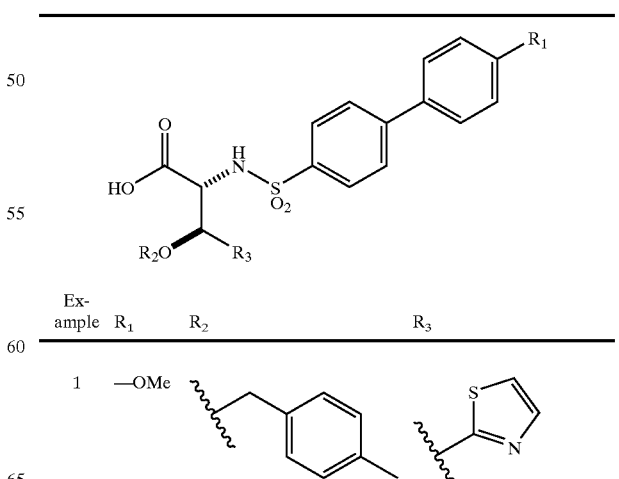

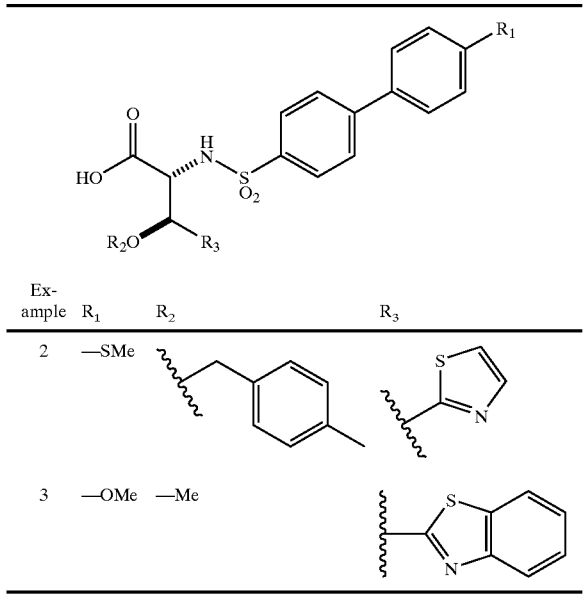

| Example | R₁ | R₂ | R₃ |
|---|---|---|---|
| 2 | —SMe | 4-methylbenzyl | thiazol-2-yl |
| 3 | —OMe | —Me | benzothiazol-2-yl |

Example 1

(2R,3S)-2-(4'-Methoxy-biphenyl-4-sulfonylamino)-3-(4-methyl-benzyloxy)-3-thiazol-2-yl-propionic Acid a) 4-(Hydroxy-thiazol-2-yl-methyl)-2,2-dimethyl-oxazolidine-3-carboxylic acid tert-butyl ester. A solution of (S)-4-formyl-2,2-dimethyl-oxazolidine-3-carboxylic acid tert-butyl ester (4.86 g, 21.2 mmol) in dichloromethane (100 mL) is stirred at room temperature and then 2-(trimethylsilyl)thiazole (5.0 g, 31.8 mmol) in dichloromethane (30 mL) is added dropwise over 30 minutes. The resulting mixture is stirred at room temperature overnight. The solvent is removed under reduced pressure and the mixture is then treated with 1N tetrabutylammonium fluoride in THF (31.8 mL, 31.8 mmol). The resulting mixture is stirred at room temperature for 1 hour and then the solvent is removed under reduced pressure. Saturated NaHCO₃ solution is added and the resulting mixture is extracted with EtOAc. The organic extracts are dried (Na₂SO₄) and then concentrated to an oil under reduced pressure. The product is purified by chromatography on silica gel using 8/2 hexane/EtOAc to provide the desired product as a white solid.

b) 2,2-Dimethyl-4-[(4-methyl-benzyloxy)-thiazol-2-yl-methyl]-oxazolidine-3-carboxylic acid tert-butyl ester. The 4-(hydroxy-thiazol-2-yl-methyl)-2,2-dimethyl-oxazolidine-3-carboxylic acid tert-butyl ester 1a (3.95 g, 12.6 mmol) in DME (100 mL) is stirred at room temperature and then sodium hydride (0.55 g, 13.9 mmol, 1.1 equiv) is added. The mixture is stirred for 15 minutes at room temperature and then 4-methylbenzyl bromide (2.57 g, 13.9 mmol, 1.1 equiv) is added. The resulting mixture is stirred at room temperature overnight and then the reaction is quenched by the addition of saturated NaHCO₃ solution (20 mL). The mixture is poured into water and then extracted with methylene chloride. The organic extracts are dried (Na₂SO₄) and then concentrated to an oil under reduced pressure. Purification of the oil is accomplished by chromatography on silica gel using 9/1 hexane/EtOAc as the eluent to provide the desired product as a colorless oil.

c) (2S,3S)-2-Amino-3-(4-methyl-benzyloxy)-3-thiazol-2-yl-propan-1-ol. The 2,2-dimethyl-4-[(4-methyl-benzyloxy)-thiazol-2-yl-methyl]-oxazolidine-3-carboxylic acid tert-butyl ester 1b (5.05 g, 12.06 mmol) in methanol (100 mL) is stirred at room temperature and then Amberlyst 15 (10 g) is added. The resulting heterogeneous mixture is stirred at room temperature for 24 hours. The mixture is treated with triethylamine (30 mL) and then stirred at room temperature for 1 hour. The resulting mixture is filtered through celite with the aid of methanol. The solvent is then removed to leave the desired product as a tan oil d) (2S,3S)-4-Bromo-N-[1-hydroxymethyl-2-(4-methyl-benzyloxy)-2-thiazol-2-yl-ethyl]-benzenesulfonamide. The (2S,3S)-2-amino-3-(4-methyl-benzyloxy)-3-thiazol-2-yl-propan-1-ol 1c (3.05 g, 10.9 mmol) in dioxane (40 mL) and water (40 mL) is stirred at room temperature and then triethylamine (2.20 g, 21.8 mmol) followed by 4-bromobenzenesulfonyl chloride (3.06 g, 11.9 mmol) are added. The resulting mixture is stirred at room temperature overnight. The reaction is diluted with 1N HCl and then extracted with methylene chloride. The organic extracts are dried and then concentrated to an oil under reduced pressure.

e) (2R,3S)-2-(4-Bromo-benzenesulfonylamino)-3-(4-methyl-benzyloxy)-3-thiazol-2-yl-propionic acid methyl ester. The (2S,3S)-4-bromo-N-[1-hydroxymethyl-2-(4-methyl-benzyloxy)-2-thiazol-2-yl-ethyl]-benzenesulfonamide 1d (3.05 g, 6.13 mmol) in acetone (50 mL) is stirred at room temperature and then the Jones reagent (8N, 30 mL, excess) is slowly added. The resulting mixture is stirred at room temperature for 3 hours and then the reaction is quenched by the addition of isopropanol. A green precipitate forms after the mixture is stirred for 30 minutes. The solution is then filtered through celite with the aid of acetone. The filtrate is concentrated to an oil under reduced pressure. The oil is dissolved in methanol and then an ethereal solution of diazomethane is added. The mixture becomes slightly yellow when excess diazomethane is added. The mixture is concentrated to a light yellow solid. Purification of the solid is accomplished by chromatography on silica gel using 8/2 hexane/EtOAc as the eluent to provide the product as a yellow solid.

f) (2R,3S)-2-(4'-Methoxy-biphenyl-4-sulfonylamino)-3-(4-methyl-benzyloxy)-3-thiazol-2-yl-propionic acid methyl ester. The (2R,3S)-2-(4-bromo-benzenesulfonylamino)-3-(4-methyl-benzyloxy)-3-thiazol-2-yl-propionic acid methyl ester 1e (590 mg, 1.12 mmol) and 4-methoxyphenylboronic acid (260 mg, 1.68 mmol) are taken up in 10 mL of benzene, 1.5 mL of EtOH and 1.5 mL of water in the presence of Pd(PPh₃)₄ (40 mg, 0.03 mmol) and 237 mg of Na₂CO₃ and brought to reflux for 18 hours. The mixture is cooled to room temperature, poured into water, and extracted with methylene chloride. The organic layer is dried over Na₂SO₄, filtered and evaporated. The crude product is purified by silica gel chromatography using 6/4 hexane/EtOAc to give the desired product as a colorless oil.

g) (2R,3S)-2-(4'-Methoxy-biphenyl-4-sulfonylamino)-3-(4-methyl-benzyloxy)-3-thiazol-2-propionic acid. The (2R,3S)-2-(4'-methoxy-biphenyl-4-sulfonylamino)-3-(4-methyl-benzyloxy)-3-thiazol-2-yl-propionic acid methyl ester 1f (550 mg, 1.00 mmol) is dissolved in water/methanol/THF (5 mL/5mL/5mL) and then lithium hydroxide (1 g, excess) is added. The resulting mixture is stirred overnight at room temperature. The reaction is acidified with 1N HCl and then the product precipitates out of solution to form a white powder. The product is filtered and the desired product is obtained as a white powder.

Example 2

(2R,3S)-3-(4-Methyl-benzyloxy)-2-(4'-methylsulfanyl-biphenyl-4-sulfonylamino)-3-thiazol-2-yl-propionic Acid a) (2R,3S)-3-(4-Methyl-benzyloxy)-2-(4'-methylsulfanyl-biphenyl-4-sulfonylamino)-3-thiazol-2-yl-propionic acid methyl ester. The (2R,3S)-2-(4-bromo-benzenesulfonylamino)-3-(4-methyl-benzyloxy)-3-thiazol-2-yl-propionic acid methyl ester 1e (660 mg, 1.26 mmol) and 4-thiomethoxyphenylboronic acid (320 mg, 1.88 mmol) are taken up in 10 mL of benzene, 1.5 mL of EtOH and 1.5 mL of water in the presence of Pd(PPh$_3$)$_4$ (44 mg, 0.03 mmol) and 267 mg of Na$_2$CO$_3$ and brought to reflux for 4 hours. The mixture is cooled to room temperature, poured into water, and extracted with methylene chloride. The organic layer is dried over Na$_2$SO$_4$, filtered and evaporated. The crude product is purified by silica gel chromatography using 8/2 hexane/EtOAc to give the desired product as a colorless oil.

b) (2R,3S)-3-(4-Methyl-benzyloxy)-2-(4'-methylsulfanyl-biphenyl-4-sulfonylamino)-3-thiazol-2-yl-propionic acid. The (2R,3S)-3-(4-methyl-benzyloxy)-2-(4'-methylsulfanyl-biphenyl-4-sulfonylamino)-3-thiazol-2-yl-propionic acid methyl ester 2a (500 mg, 0.88 mmol) is dissolved in water/methanol/THF (5 mL/5 mL/5 mL) and then lithium hydroxide (1 g, excess) is added. The resulting mixture is stirred overnight at room temperature. The reaction is acidified with 1N HCl and the product crashes out of solution. The product (345 mg) is obtained as a white powder.

Example 3

(2R,3S)-3-Benzothiazol-2-yl-3-metboxy-2-(4'-methoxy-biphenyl-4-sulfonylamino)-proionic Acid a) 4-(Benzotbiazol-2-yl-hydroxy-metbyl)-2,2-dimethyl-oxazolidine-3-carboxylic acid tert-butyl ester. A solution of (S)-4-formyl-2,2-dimethyl-oxazolidine-3-carboxylic acid tert-butyl ester (7.37 g, 32.1 mmol) in dichloromethane (150 mL) is stirred at room temperature and then 2-(trimethylsilyl)benzothiazole (10.0 g, 48.2 mmol) in dichloromethane (30 mL) is added dropwise over 30 minutes. The resulting mixture is stirred at room temperature overnight. The solvent is removed under reduced pressure and the mixture is then treated with 1N tetrabutylammonium fluoride in THF (48 mL, 48 mmol). The resulting mixture is stirred at room temperature for 1 hour and then the solvent is removed under reduced pressure. Saturated NaHCO$_3$ solution is added and the resulting mixture is extracted with EtOAc. The organic extracts are dried (Na$_2$SO$_4$) and then concentrated to an oil under reduced pressure. The product is purified by chromatography on silica gel using 85/15 hexane/EtOAc to provide the desired product as a white solid.

b) 4-(Benzothiazol-2-yl-methoxy-methyl)-2,2-dimethyl-oxazolidine-3-carboxylic acid tert-butyl ester. The 4-(benzothiazol-2-yl-hydroxy-methyl)-2,2-dimethyl-oxazolidine-3-carboxylic acid tert-butyl ester 3a (3.40 g, 9.30 mmol) in DME (75 mL) is stirred at room temperature and then sodium hydride (60%, 0.45 g, 11.2 mmol, 1.1 equiv) is added. The mixture is stirred for 15 minutes at room temperature and then methyl iodide (1.45 g, 10.2 mmol, 1.1 equiv) is added. The resulting mixture is stirred at room temperature overnight and then the reaction is quenched by the addition of saturated NaHCO$_3$ solution (20 mL). The mixture is poured into water and then extracted with methylene chloride. The organic extracts are dried (Na$_2$SO$_4$) and then concentrated to an oil under reduced pressure. Purification of the oil is accomplished by chromatography on silica gel using 8/2 hexane/EtOAc as the eluent to provide the desired product as a colorless oil.

c) (2S,3S)-2-Amino-3-benzothiazol-2-yl-3-methoxy-propan-1-ol. The 4-(benzothiazol-2-yl-methoxy-methyl)-2,2-dimethyl-oxazolidine-3-carboxylic acid tert-butyl ester 3b (2.00 g, 5.28 mmol) in methanol (100 mL) is stirred at room temperature and then Amberlyst 15 (5 g) is added. The resulting heterogeneous mixture is stirred at room temperature for 24 hours. The mixture is treated with triethylamine (25 mL) and then stirred at room temperature for 1 hour. The resulting mixture is filtered through celite with the aid of methanol. The solvent is then removed to leave the desired product as a tan oil d) (2S,3S)-N-(2-Benzothiazol-2-yl-1-hydroxymethyl-2-methoxy-ethyl)-4-bromo-benzenesulfonamide. The (2S,3S)-2-amino-3-benzothiazol-2-yl-3-methoxy-propan-1-ol 3c (1.0 g, 4.20 mmol) in dioxane (20 mL) and water (20 mL) is stirred at room temperature and then triethylamine (0.85 g, 8.40 mmol) followed by 4-bromobenzenesulfonyl chloride (1.18 g, 4.6 mmol) are added. The resulting mixture is stirred at room temperature overnight. The reaction is diluted with 1N HCl and then extracted with methylene chloride. The organic extracts are dried and then concentrated to an oil under reduced pressure.

e) (2S,3S)-4'-Methoxy-biphenyl-4-sulfonic acid (2-benzothiazol-2-yl-1-hydroxymethyl-2-methoxy-ethyl)-amide. The (2S,3S)-N-(2-benzothiazol-2-yl-1-hydroxymethyl-2-methoxy-ethyl)-4-bromo-benzenesulfonamide 3d (505 mg, 1.10 mmol) and 4-methoxyphenylboronic acid (252 mg, 1.65 mmol) are taken up in 10 mL of benzene, 1.5 mL of EtOH and 1.5 mL of water in the presence of Pd(PPh$_3$)$_4$ (38 mg, 0.03 mmol) and 225 mg of Na$_2$CO$_3$ and brought to reflux for 18 hours. The mixture is cooled to room temperature, poured into water, and extracted with methylene chloride. The organic layer is dried over Na$_2$SO$_4$, filtered and evaporated. The crude product is purified by silica gel chromatography using 6/4 hexane/EtOAc to give the desired product as a colorless oil.

f) (2R,3S)-3-Benzothiazol-2-yl-3-methoxy-2-(4'-methoxy-biphenyl-4-sulfonylamino)-proionic acid. The (2S,3S)-4'-methoxy-biphenyl-4-sulfonic acid (2-benzothiazol-2-yl-1-hydroxymethyl-2-methoxy-ethyl)-amide 3e (400 mg) in acetone (50 mL) is stirred at room temperature and then the Jones reagent (8N, 15 mL, excess) is slowly added. The resulting mixture is stirred at room temperature for 3 hours and then the reaction is quenched by the addition of isopropanol. A green precipitate forms after the mixture is stirred for 30 minutes. The solution is then filtered through celite with the aid of acetone. The filtrate is concentrated to an oil under reduced pressure. The oil is dissolved in methanol and then an ethereal solution of diazomethane is added. The mixture becomes slightly yellow when excess diazomethane is added. The mixture is concentrated to a light yellow solid. Purification of the solid is accomplished by chromatography on silica gel using 8/2 hexane/EtOAc as the eluent to provide the product as a white solid.

Examples 4–36

The following chart shows the structure of compounds made according to the description in Examples 4–36 described below:

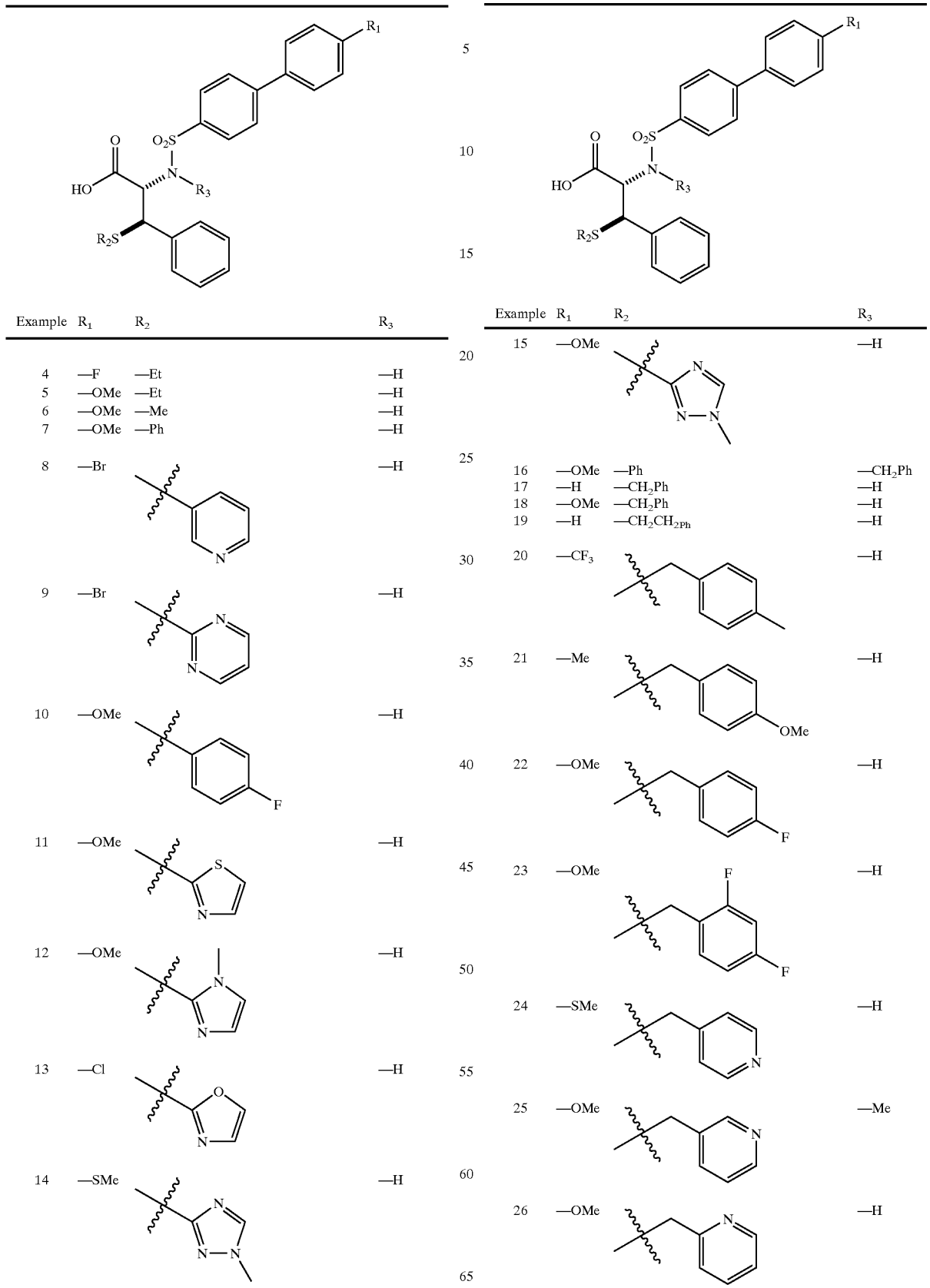

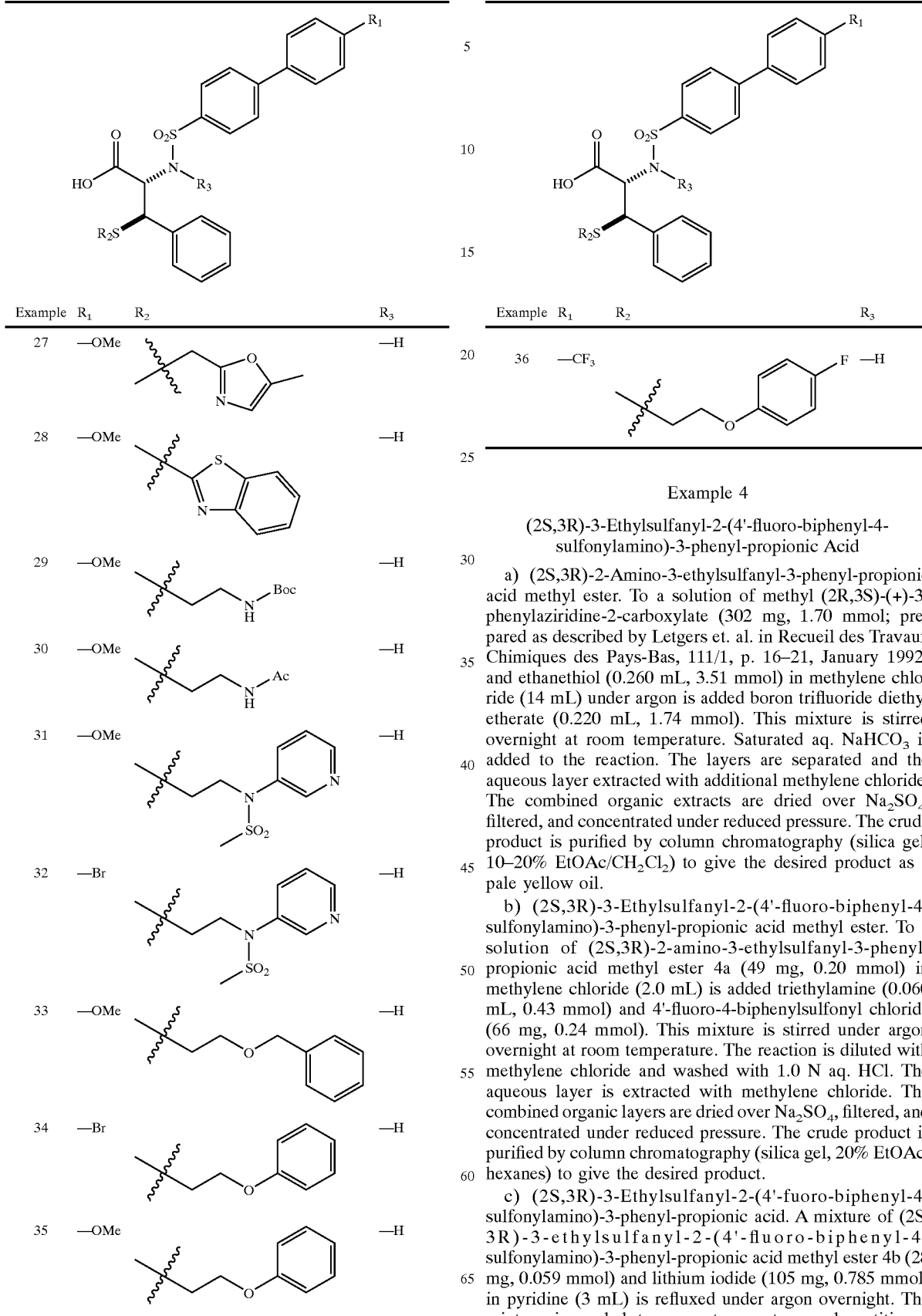

Example 4

(2S,3R)-3-Ethylsulfanyl-2-(4'-fluoro-biphenyl-4-sulfonylamino)-3-phenyl-propionic Acid a) (2S,3R)-2-Amino-3-ethylsulfanyl-3-phenyl-propionic acid methyl ester. To a solution of methyl (2R,3S)-(+)-3-phenylaziridine-2-carboxylate (302 mg, 1.70 mmol; prepared as described by Letgers et. al. in Recueil des Travaux Chimiques des Pays-Bas, 111/1, p. 16–21, January 1992) and ethanethiol (0.260 mL, 3.51 mmol) in methylene chloride (14 mL) under argon is added boron trifluoride diethyl etherate (0.220 mL, 1.74 mmol). This mixture is stirred overnight at room temperature. Saturated aq. NaHCO$_3$ is added to the reaction. The layers are separated and the aqueous layer extracted with additional methylene chloride. The combined organic extracts are dried over Na$_2$SO$_4$, filtered, and concentrated under reduced pressure. The crude product is purified by column chromatography (silica gel, 10–20% EtOAc/CH$_2$Cl$_2$) to give the desired product as a pale yellow oil.

b) (2S,3R)-3-Ethylsulfanyl-2-(4'-fluoro-biphenyl-4-sulfonylamino)-3-phenyl-propionic acid methyl ester. To a solution of (2S,3R)-2-amino-3-ethylsulfanyl-3-phenyl-propionic acid methyl ester 4a (49 mg, 0.20 mmol) in methylene chloride (2.0 mL) is added triethylamine (0.060 mL, 0.43 mmol) and 4'-fluoro-4-biphenylsulfonyl chloride (66 mg, 0.24 mmol). This mixture is stirred under argon overnight at room temperature. The reaction is diluted with methylene chloride and washed with 1.0 N aq. HCl. The aqueous layer is extracted with methylene chloride. The combined organic layers are dried over Na$_2$SO$_4$, filtered, and concentrated under reduced pressure. The crude product is purified by column chromatography (silica gel, 20% EtOAc/hexanes) to give the desired product.

c) (2S,3R)-3-Ethylsulfanyl-2-(4'-fuoro-biphenyl-4-sulfonylamino)-3-phenyl-propionic acid. A mixture of (2S,3R)-3-ethylsulfanyl-2-(4'-fluoro-biphenyl-4-sulfonylamino)-3-phenyl-propionic acid methyl ester 4b (28 mg, 0.059 mmol) and lithium iodide (105 mg, 0.785 mmol) in pyridine (3 mL) is refluxed under argon overnight. The mixture is cooled to room temperature and partitioned between ethyl acetate and 1.0 N aq. HCl. The organic layer is dried over $Na_2SO_4$, filtered, and concentrated under reduced pressure. The crude product is purified by reverse phase preparative HPLC (gradient elution, 0.1% aq. trifluoroacetic acid/acetonitrile) to give the desired product as a pale orange solid.

Example 5

(2S,3R)-3-Ethylthio-2-[(4'-methoxyl[1,1'-biphenyl]-4-yl)sulfonyl]amino)-3-phenyl-propionic Acid a) Methyl (2S,3R)-3-ethylthio-2-[(4-iodophenyl]sulfonyl]amino)-3-phenyl-propanoate. To a solution of methyl (2S,3R)-2-amino-3-ethylthio-3-phenyl-propionate 4a (248 mg, 1.04 mmol) in methylene chloride is added triethylamine (0.290 mL, 2.08 mmol). This mixture is cooled to 0° C. and treated dropwise with a solution of pipsyl chloride (378 mg, 1.25 mmol) in methylene chloride (1 mL). This mixture is stirred under argon overnight while warming from 0° C. to room temperature. The mixture is diluted with methylene chloride and washed with 1.0 N aq. HCl. The aqueous layer is extracted with methylene chloride. The combined organic extracts are dried over $Na_2SO_4$, filtered, and concentrated under reduced pressure. The crude product is purified by column chromatography (silica gel, 15% EtOAc/hexanes) to give the desired product.

b) Methyl (2S,3R)-3-ethylthio-2-[(4'-methoxyl[1,1'-biphenyl]-4-yl)sulfonyl]amino)-3-phenyl-propionate. To a solution of methyl (2S,3R)-3-ethylthio-2-[(4-iodophenyl]sulfonyl]amino)-3-phenyl-propanoate 5a (376 mg, 0.744 mmol) in benzene (5.0 mL) is added sodium carbonate (158 mg, 1.49 mmol), water (0.75 mL), tetrakis(triphenylphosphine)palladium (0) (25 mg, 0.022 mmol), and last a solution of 4-methoxyphenylboronic acid (166 mg, 1.09 mmol) in methanol (0.75 mL). This mixture is refluxed under argon for 24 hr. The mixture is cooled to room temperature, treated with 35 wt. % hydrogen peroxide (0.300 mL), and stirred for 0.25 hr. The reaction is diluted with water and extracted with diethyl ether three times. The combined organic extracts are dried over $Na_2SO_4$, filtered, and concentrated under reduced pressure. The crude product is purified by column chromatography (silica gel, 15–30% EtOAc/hexanes) to give the desired product as a pale yellow solid.

c) (2S,3R)-3-Ethylthio-2-[(4'-methoxyl[1,1'-biphenyl]-4-yl)sulfonyl]amino)-3-phenyl-propionic acid. The title compound is prepared from 5b using ester hydrolysis conditions analogous to the preparation of Example 4.

Examples 6–36

Examples 6–36 are prepared from the corresponding thiol and S2e using procedures described for Example 4 or 5.

Example 37

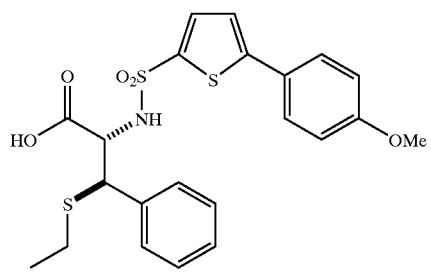

(2S,3R)-3-Ethylsulfanyl-2-[5-(4-methoxy-phenyl)-thiophene-2-sulfonylamino]-3-phenyl-propionic acid This compound is prepared according to the procedures described for Example 5 using 5-bromothiofenyl sulfonyl chloride in place of pipsyl chloride.

Example 38

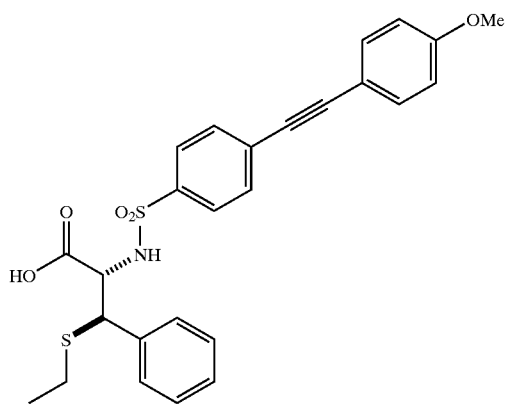

(2S,3R)-3-Ethylsulfanyl-2-[4-(4-methoxy-phenylethynyl)-benzenesuffonylamino]-3-phenyl-propionic acid This compound is prepared according to the procedures described for Example 5 using 4-methoxyphenylacetylene boronic acid in place of 4-methoxyphenyl boronic acid.

Example 39

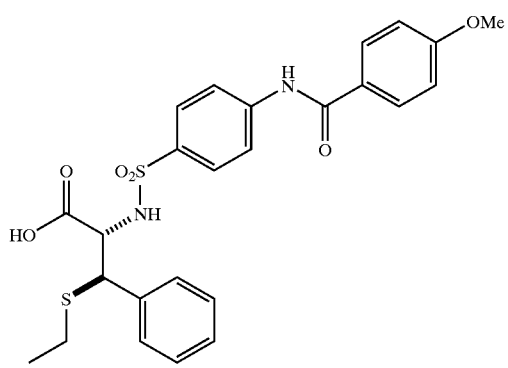

(2S,3R)-3-Ethylsulfanyl-2-[4-(4-methoxy-benzoylamino)-benzenesulfonylamino]-3-phenyl-propionic acid This compound is prepared according to the procedures described for Example 5 using 4-nitrobenzene sulfonyl chloride in place of pipsyl chloride, followed by 1) reduction of the nitro group by tin (II) chloride, and 2) amide formation with 4-methoxybenzoyl chloride.

Examples 40–43

The folowing chart shows the structure of compounds made according to the description in Examples 40–43 described below:

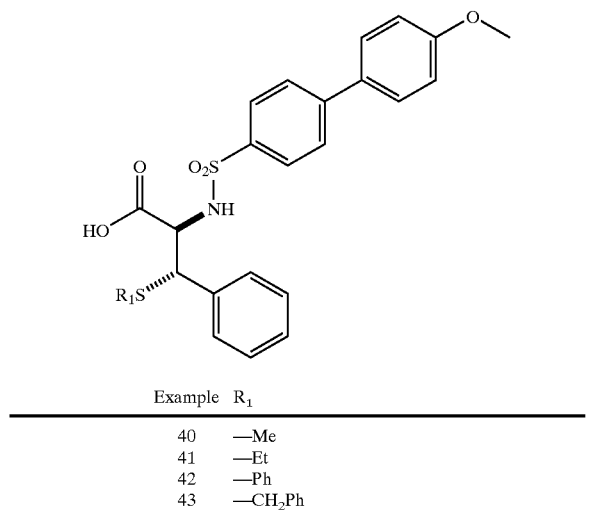

| Example | R$_1$ |
|---|---|
| 40 | —Me |
| 41 | —Et |
| 42 | —Ph |
| 43 | —CH$_2$Ph |

Examples 40–43

Examples 40–43 are prepared from methyl (2S,3R)-(−)-3-phenylaziridine-2-carboxylate using procedures described for Example 4 or 5.

Examples 44–68

The following chart shows the structure of compounds made according to the description in Examples 44–68 described below:

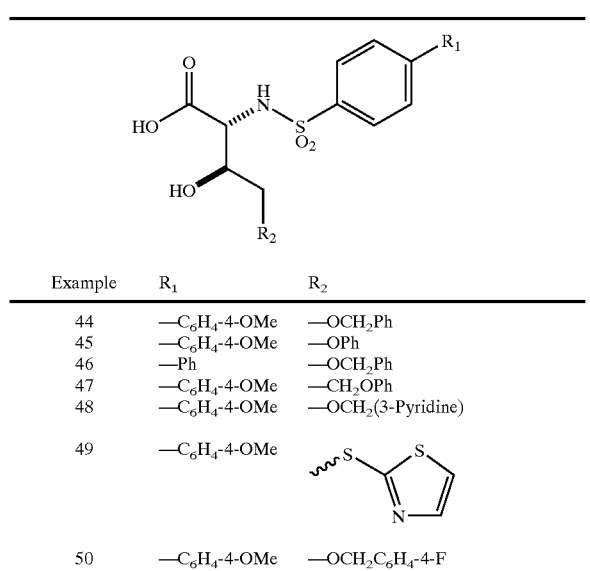

| Example | R$_1$ | R$_2$ |
|---|---|---|
| 44 | —C$_6$H$_4$-4-OMe | —OCH$_2$Ph |
| 45 | —C$_6$H$_4$-4-OMe | —OPh |
| 46 | —Ph | —OCH$_2$Ph |
| 47 | —C$_6$H$_4$-4-OMe | —CH$_2$OPh |
| 48 | —C$_6$H$_4$-4-OMe | —OCH$_2$(3-Pyridine) |
| 49 | —C$_6$H$_4$-4-OMe | (thiazol-2-ylthio) |
| 50 | —C$_6$H$_4$-4-OMe | —OCH$_2$C$_6$H$_4$-4-F |

-continued

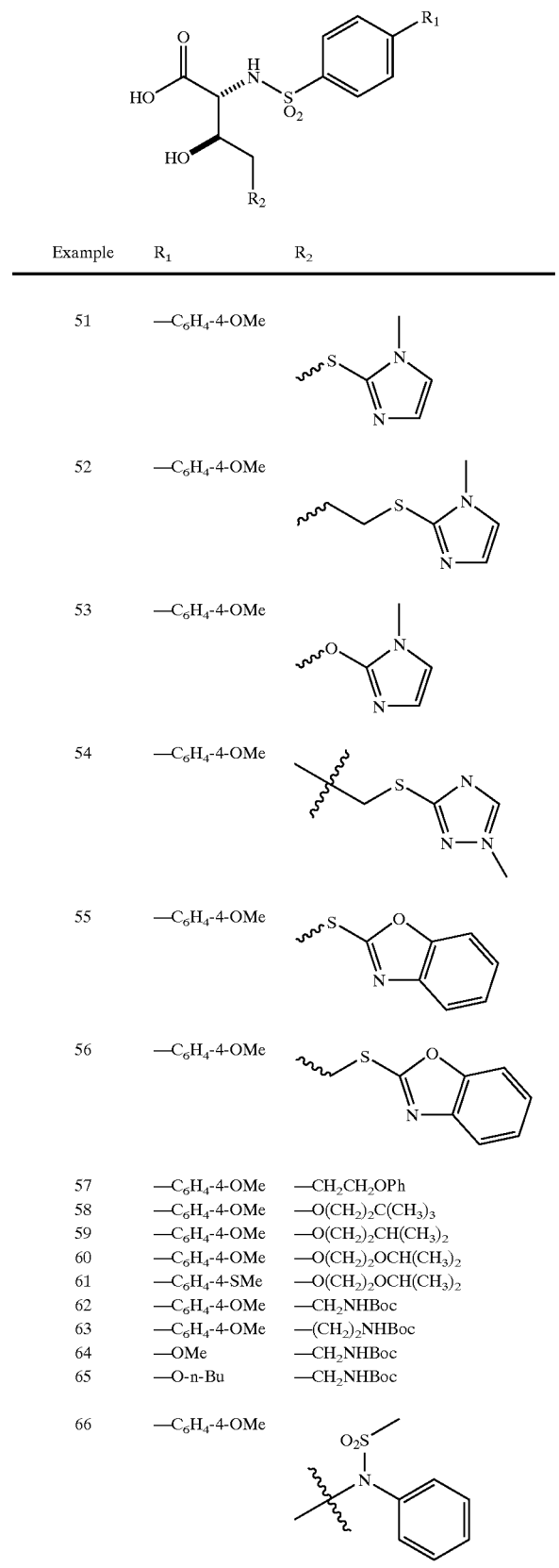

| Example | R$_1$ | R$_2$ |
|---|---|---|
| 51 | —C$_6$H$_4$-4-OMe | (1-methylimidazol-2-ylthio) |
| 52 | —C$_6$H$_4$-4-OMe | (1-methylimidazol-2-ylthioethyl) |
| 53 | —C$_6$H$_4$-4-OMe | (1-methylimidazol-2-yloxy) |
| 54 | —C$_6$H$_4$-4-OMe | (1-methyl-1,2,4-triazol-3-ylthiomethyl) |
| 55 | —C$_6$H$_4$-4-OMe | (benzoxazol-2-ylthio) |
| 56 | —C$_6$H$_4$-4-OMe | (benzoxazol-2-ylthiomethyl) |
| 57 | —C$_6$H$_4$-4-OMe | —CH$_2$CH$_2$OPh |
| 58 | —C$_6$H$_4$-4-OMe | —O(CH$_2$)$_2$C(CH$_3$)$_3$ |
| 59 | —C$_6$H$_4$-4-OMe | —O(CH$_2$)$_2$CH(CH$_3$)$_2$ |
| 60 | —C$_6$H$_4$-4-OMe | —O(CH$_2$)$_2$OCH(CH$_3$)$_2$ |
| 61 | —C$_6$H$_4$-4-SMe | —O(CH$_2$)$_2$OCH(CH$_3$)$_2$ |
| 62 | —C$_6$H$_4$-4-OMe | —CH$_2$NHBoc |
| 63 | —C$_6$H$_4$-4-OMe | —(CH$_2$)$_2$NHBoc |
| 64 | —OMe | —CH$_2$NHBoc |
| 65 | —O-n-Bu | —CH$_2$NHBoc |
| 66 | —C$_6$H$_4$-4-OMe | (N-methylsulfonyl-N-phenylamino) |

-continued

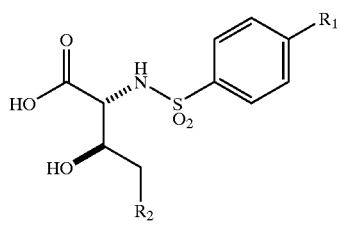

| Example | R₁ | R₂ |
|---|---|---|
| 67 | —C₆H₄-4-OMe | |
| 68 | —C₆H₄-4-OMe | —O(CH₂)₂NHBoc |

Example 44

(2R,3S)-4-Benzloxy-3-hydroxy-2-(4'-methoxy-biphenyl-4-sulfonylamino)-butyric Acid (a) 4(S)-Benzyl-3-[(2S, 3R)-4-benzyloxy-2-bromo-3-hydroxy-butyryl]-oxazolidin-2-one. A solution of 4(S)-Benzyl-3-(2-bromo-acetyl)-oxazolidin-2-one (1.621 g, 5.43 mmol, prepared as described previously (J. Am. Chem. Soc. 1986, 108, 4595) in ether (25 mL) is cooled to −78° C. and triethylamine (770 mg, 7.61 mmol) is added followed by dibutylboron triflate (1.84 g, 5.98 mmol). The cooling bath is removed and the reaction mixture is stirred for 2.5 hr. The reaction mixture is cooled to −78° C., benzyloxyacetaldehyde (898 mg, 5.98 mmol) is added and, after stirring for 10 min, the mixture is warmed up to 0° C. and stirred for 3 hr. The reaxtion mixture is diluted with ether, washed with 1N aq KHSO₄ and solvents are removed under vacum. The residue is dissolved in methanol (10 mL), cooled to 0° C. and 30% hydrogen peroxide (5 mL) is added. The cooling bath is removed and the mixture is stirred at room temperature for 2 hr. Saturated aq. NaHCO₃ and methylene chloride are added to the reaction mixture. The layers are separated and the aqueous layer extracted with additional methylene chloride. The combined organic extracts are dried over Na₂SO₄, filtered, and concentrated under reduced pressure. The crude product is purified by column chromatography (silica gel, 1% MeOH/CH₂Cl₂) to give the desired product as a light yellow oil.

(b) 4(S)-3-[(2R, 3S)-2-Azido-4-benzyloxy-3-hydroxy-butyryl]-4-benzyl-oxazolidin-2-one. To a solution of 4(S)-benzyl-3-[(2S, 3R)-4-benzyloxy-2-bromo-3-hydroxy-butyryl]-oxazolidin-2-one (969 mg, 2.16 mmol) in dimethylformamide (9.0 mL) is added sodium azide (211 mg, 3.25 mmol) and the reaction mixture is stirred at 35° C. for 4 hr. The mixture is diluted with ethyl acetate and washed several times with water, brine and dried over Na₂SO₄. Filtration and removal of solvents under vacuo gives 4(S)-3-[(2R, 3R)-2-azido-4-benzyloxy-3-hydroxy-butyryl)]-4-benzyl-oxazolidin-2-one as an oil.

(c) (2R, 3S)-2-Azido-4-benzyloxy-3-hydroxy-butyric acid. To a solution of 4(S)-3-[(2R, 3S)-2-azido-4-benzyloxy-3-hydroxy-butyryl]-4-benzyl-oxazolidin-2-one (500 mg, 1.2 mmol) in dioxane-water (3.5 mL, 6:1, v/v) cooled to 0° C. is added a solution of lithium hydroxide hydrate (113 mg, 2.7 mmol) in water (1.5 mL) and the reaction mixture is stirred at room temperature for 2 hr. A solution of 1N hydrogen chloride (4 mL) is then added and solvents are removed under reduced pressure. The residue is dissolved in methylene chloride and the organic phase is washed with water, brine and dried over Na₂SO₄. Filtration and removal of solvents under vacuum gives (2R, 3S)-2-azido-4-benzyloxy-3-hydroxy-butyric acid as a thick oil.

(d) (2R,3S)-4-Benzyloxy-3-hydroxy-2-(4'-methoxy-biphenyl-4-sulfonylamino)-butyric acid. To a solution of (2R, 3S)-2-azido-4-benzyloxy-3-hydroxy-butyric acid (50 mg) in methanol (1 mL) is added tin (II) chloride (60 mg) and the reaction mixture is stirred at room temperature for 2 hr. The volatiles are removed under vacuum and the residue is dissolved in dioxane-water (1.6 mL, 1:1, v/v). To the mixture is added triethylamine (0.1 mL) and (4'-methoxy[1, 1'-biphenyl]-4-yl)sulfonyl chloride (110 mg) and the mixture is stirred at room temperature for 10 hr. The volatiles are removed under vacuum and the residue is treated with methanol (3 mL) and acetic acid (1 mL). The precipitate is filtered off, the filtrate is concentrated and a crude product is purified using RF HPLC to give (2R,3R)-4-benzyloxy-3-hydroxy-2-(4'-methoxy-biphenyl-4-sulfonylamino)-butyric acid as a white, crystalline solid.

Examples 45–68

Example 45–68 are prepared using a corresponding aldehyde and S3a following the procedure described for Example 44.

IX. EXAMPLES

Compositions and Methods of Use

The compounds of the invention are useful to prepare compositions for the treatment of ailments associated with unwanted MP activity. The following composition and method examples do not limit the invention, but provide guidance to the skilled artisan in preparing and using the compounds, compositions and methods of the invention. In each case, other compounds within the invention may be substituted for the example compound shown below to provide substantially similar results. The skilled practitioner will appreciate that the examples provide guidance and may be varied based on the condition being treated and the patient.

The following abbreviations are used:
EDTA: ethylenediaminetetracetic acid
SDA: synthetically denatured alcohol
USP: United States Pharmacopoeia

Example A

A tablet composition for oral administration, according to the present invention, is made comprising:

| Component | Amount |
|---|---|
| The compound of Example 1 | 15 mg |
| Lactose | 120 mg |
| Maize Starch | 70 mg |
| Talc | 4 mg |
| Magnesium Stuart | 1 mg |

A human female subject weighing 60 kg (132 lbs), suffering from rheumatoid arthritis, is treated by a method of this invention. Specifically, for 2 years, a regimen of three tablets per day is administered orally to said subject.

At the end of the treatment period, the patient is examined and is found to have reduced inflammation and improved mobility without concomitant pain.

Example B

A capsule for oral administration, according to the present invention, is made comprising:

| Component | Amount (% w/w) |
|---|---|
| The compound of Example 4 | 15% |
| Polyethylene glycol | 85% |

A human male subject weighing 90 kg (198 lbs.), suffering from osteoarthritis, is treated by a method of this invention. Specifically, for 5 years, the above capsule, which contains 70 mg of the compound of Example 4, is administered daily to said subject.

At the end of the treatment period, the patient is examined via x-ray, arthroscopy and/or MRI, and found to have no further advancement of erosion/fibrillation of the articular cartilage.

Example C

A saline-based composition for local administration, according to the present invention, is made comprising:

| Component | Amount (% w/w) |
|---|---|
| The compound of Example 7 | 5% |
| Polyvinyl alcohol | 15% |
| Saline | 80% |

A patient having deep corneal abrasion applies a drop of the composition to each eye twice a day. Healing is speeded, with no visual sequelae.

Example D

A topical composition for local administration, according to the present invention, is made comprising:

| Component | Composition (% w/v) |
|---|---|
| The compound of Example 9 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

A patient suffering from chemical burns applies the composition at each dressing change (b.i.d.). Scarring is substantially diminished.

Example E

An inhalation aerosol composition, according to the present invention, is made comprising:

| Component | Composition (% w/v) |
|---|---|
| Compound of Example 13 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

An asthma sufferer sprays 0.01 mL of the composition via a pump actuator into the mouth while inhaling. Asthma symptoms are diminished.

Example F

A topical opthalmic composition, according to the present invention, is made comprising:

| Component | Composition (% w/v) |
|---|---|
| Compound of Example 16 | 0.10 |
| Benzalkonium chloride | 0.01 |
| EDTA | 0.05 |
| Hydroxyethylcellulose (NATROSOL M) | 0.50 |
| Sodium metabisulfite | 0.10 |
| Sodium chloride (0.9%) | q.s. |
| Total = | 100.0 |

A human male subject weighing 90 kg (198 lbs), suffering from corneal ulcerations, is treated by a method of this invention. Specifically, for 2 months, a saline solution containing 10 mg of the compound of Example 16 is administered to said subject's affected eye twice-daily.

Example G

A composition for parenteral administration is made comprising:

| Component | Amount |
|---|---|
| The compound of Example 12 | 100 mg/mL carrier |
| Carrier: | |
| Sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 mL of the suspension is administered, via injection, to a human subject with a premetastatic tumor. The injection site juxtaposes the tumor. This dosage is repeated twice daily, for approximately 30 days. After 30 days, symptoms of the disease subside, and dosage is gradually decreased to maintain the patient.

Example H

A mouthwash composition is prepared:

| Component | % w/v |
|---|---|
| The compound of Example 14 | 3.0 |
| SDA 40 Alcohol | 8.0 |
| Flavor | 0.08 |
| Emulsifier | 0.08 |
| Sodium Fluoride | 0.05 |
| Glycerin | 10.0 |
| Sweetener | 0.02 |
| Benzoic acid | 0.05 |
| Sodium hydroxide | 0.20 |
| Dye | 0.04 |
| Water | balance to 100% |

A patient with gum disease uses 1 mL of the mouthwash thrice daily to prevent further oral degeneration.

Example I

A lozenge composition is prepared:

| Component | % w/v |
|---|---|
| The compound of Example 35 | 0.01 |
| Sorbitol | 17.50 |
| Mannitol | 17.50 |
| Starch | 13.60 |
| Sweetener | 1.20 |
| Flavor | 11.70 |
| Color | 0.10 |
| Corn Syrup | balance to 100% |

A patient uses the lozenge to prevent loosening of an implant in the maxilla.

Example J

A chewing gum composition is prepared, comprising the following:

| Component | w/v % |
|---|---|
| The compound of Example 55 | 0.03 |
| Sorbitol crystals | 38.44 |
| Paloja-T gum base | 20.0 |
| Sorbitol (70% aqueous solution) | 22.0 |
| Mannitol | 10.0 |
| Glycerine | 7.56 |
| Flavor | 1.0 |

A patient chews the gum to prevent loosening of dentures.

Example K

| Components | w/v % |
|---|---|
| Compound of Example 28 | 4.0 |
| USP Water | 50.656 |
| Methylparaben | 0.05 |
| Propylparaben | 0.01 |
| Xanthan Gum | 0.12 |
| Guar Gum | 0.09 |
| Calcium carbonate | 12.38 |
| Antifoam | 1.27 |
| Sucrose | 15.0 |
| Sorbitol | 11.0 |
| Glycerin | 5.0 |
| Benzyl Alcohol | 0.2 |
| Citric Acid | 0.15 |
| Coolant | 0.00888 |
| Flavor | 0.0645 |
| Colorant | 0.0014 |

The composition is prepared by first mixing 80 kg of glycerin and all of the benzyl alcohol and heating to 65° C., then slowly adding and mixing together methylparaben, propylparaben, water, xanthan gum, and guar gum. These ingredients are mixed for about 12 minutes with a Silverson in-line mixer. The following ingredients are then added in the following order: remaining glycerin, sorbitol, antifoam C, calcium carbonate, citric acid, and sucrose. The flavors and coolants are separately combined and then are slowly added to the other ingredients. The mixture is mixed for about 40 minutes. The patient takes the formulation to prevent flare up of colitis.

Example L

An obese human female subject, who is determined to be prone to osteoarthritis, is administered the capsule described in Example B to prevent the symptoms of osteoarthritis. Specifically, a capsule is administered daily to the subject.

The patient is examined via x-ray, arthroscopy and/or MRI, and found to have no significant advancement of erosion/fibrillation of the articular cartilage.

Example M

A human male subject weighing 90 kg (198 lbs.), who suffers a sports injury, is administered the capsule described in Example B to prevent the symptoms of osteoarthritis. Specifically, a capsule is administered daily to the subject.

The patient is examined via x-ray, arthroscopy and/or MRI, and found to have no significant advancement of erosion/fibrillation of the articular cartilage.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:
1. A compound having a structure according to Formula (I)

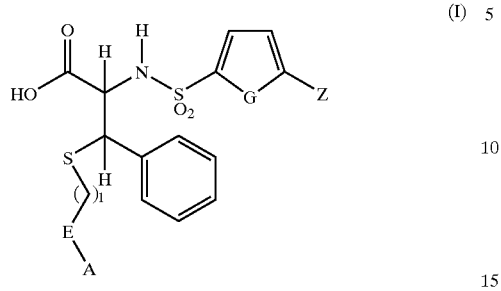

wherein:
(A) l is from 0 to about 4;
(B) E is selected from a covalent bond, —O—, —S—, —S(O)—, —S(O$_2$)—, —N(R$^{10}$)—, —N(COR$^{10}$)—, —N(CO$_2$R$^{10}$)—, —N(CONR$^{10}$R$^{10'}$)—, and —N(SO$_2$R$^{10}$)—, where (i) each R$^{10}$ and R$^{10'}$, when present, is independently selected from hydrogen, alkyl, alkenyl, alkynyl, heteroalkyl, haloalkyl, aryl, arylalkyl, heteroaryl, heteroarylalkyl, cycloalkyl, and heterocycloalkyl, or (ii) R$^{10}$ and R$^{10'}$, together with the nitrogen atom to which they are bonded, join to form an optionally substituted heterocyclic ring containing from 5 to 8 ring atoms of which from 1 to 3 are heteroatoms; provided That when l=0, E is a covalent bond; and
(C)
  (1) A is selected from hydrogen, alkyl, alkenyl, alkynyl, heteroalkyl, haloalkyl, aryl, arylalkyl, heteroaryl, heteroarylalkyl, cycloalkyl, and heterocycloalkyl; or
  (2) A, together with R$^{10}$, or R$^{10'}$, join to form an optionally substituted heterocyclic ring containing from 5 to 8 ring atoms of which from 1 to 3 are heteroatoms;
(D) G is selected from —C(R$^{11}$)=C(R$^{11'}$)—, where each R$^{11}$ and R$^{11'}$ is independently selected from hydrogen, alkyl, alkenyl, alkynyl, heteroalkyl, aryl, heteroaryl, cycloalkyl, and heterocycloalkyl;
(E) Z is selected from:
  (1) cycloalkyl and heterocycloalkyl;
  (2) —L—(CR$^{12}$R$^{12'}$)$_a$—R$^{13}$ where:
    (a) a is from 0 to about 4;
    (b) L is selected from —C≡C—, —CH=CH—, —N=N—, —O—, —S— and —SO$_2$—;
    (c) each R$^{12}$ and R$^{12'}$, when present, is independently selected from alkyl, alkenyl, alkynyl, aryl, heteroalkyl, heteroaryl, cycloalkyl, heterocycloalkyl, halogen, haloalkyl, hydroxy, and alkoxy; and
    (d) R$^{13}$ is selected from hydrogen, aryl, heteroaryl, alkyl, alkenyl, alkynyl, heteroalkyl, haloalkyl, heterocycloalkyl and cycloalkyl; and, if L is —C≡C— or —CH=CH—, then R$^{13}$ may also be selected from —CON(R$^{14}$R$^{14'}$) where (i) R$^{14}$ and R$^{14'}$ are independently selected from hydrogen, alkyl, alkenyl, alkynyl, haloalkyl, heteroalkyl, aryl, heteroaryl, cycloalkyl, and heterocycloalkyl, or (ii) R$^{14}$ and R$^{14'}$, together with the nitrogen atom to which they are bonded, join to form an optionally substituted heterocyclic ring containing from 5 to 8 ring atoms of which from 1 to 3 are heteroatoms;
  (3) —NR$^{15}$R$^{15'}$ where:
    (a) R$^{15}$ and R$^{15'}$ each is independently selected from hydrogen, alkyl, alkenyl, alkynyl, heteroalkyl, haloalkyl, aryl, heteroaryl, cycloalkyl, heteroalkyl and —C(O)—Q—(CR$^{16}$R$^{16'}$)$_b$—R$^{17}$ where:
      (i) b is from t to about 4;
      (ii) Q is selected from a covalent bond and —N(R$^{18}$)—; and
      (iii) each R$^{16}$ and R$^{16'}$, when present, is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; each R$^{17}$ and R$^{18}$ is independently selected from hydrogen, alkyl alkenyl, alkynyl, heteroalkyl, haloalkyl, aryl, heteroaryl, cycloalkyl, and heterocycloalkyl, or R$^{17}$ and R$^{18}$, together with the atoms to which they are bonded, join to form an optionally substituted heterocyclic ring containing from 5 to 8 ring atoms of which from 1 to 3 are heteroatoms; or R$^{15}$ and R$^{18}$, together with the nitrogen atoms to which they are bonded, join to form an optionally substituted heterocyclic ring containing from 5 to 8 ring atoms of which from 2 to 3 are heteroatoms; or
    (b) R$^{15}$ and R$^{15'}$, together with the nitrogen atom to which they are bonded, join to form an optionally substituted heterocyclic ring containing from 5 to 8 ring atoms of which from 1 to 3 are heteroatoms; and
  (4)

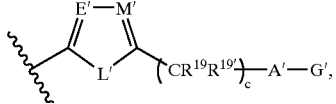

where:
  (a) E' and M' are independently selected from —C— and —N—;
  (b) L' is selected from —S—, —O—, —N(R$^{20}$)—, —C(R$^{20}$)=C(R$^{20'}$)—, —N=C(R$^{20}$)—, and —N=N—, where each R$^{20}$ and R$^{20'}$, when present, is independently selected from hydrogen, alkyl, alkenyl, alkynyl, heteroalkyl, aryl, heteroaryl, cycloalkyl, and heterocycloalkyl;
  (c) c is from 0 to about 4;
  (d) each R$^{19}$ and R$^{19'}$, when present, is independently selected from hydrogen, alkyl, alkenyl, alkynyl, aryl, heteroalkyl, heteroaryl, cycloalkyl, heterocycloalkyl, halogen, haloalkyl, hydroxy, and alkoxy;
  (e) A' is selected from a covalent bond, —O—, —SO$_d$——C(O)—, —C(O)N(R$^{21}$)—, —N(R$^{21}$)—, and —N(R$^{21}$)C(O)—; where d is from 0 to 2 and R$^{21}$ is selected from hydrogen, alkyl, alkenyl, alkynyl, aryl, heteroaryl, heteroalkyl, heteroaryl, cycloalkyl, heterocycloalkyl, and haloalkyl: and
  (f) G' is —(CR$^{22}$R$^{22'}$)$_e$—R$^{23}$ where e is from 0 to about 4; each R$^{22}$ and R$^{22'}$, when present, is independently selected from hydrogen, alkyl, alkenyl, alkynyl, aryl, heteroalkyl, heteroaryl, cycloalkyl, heterocycloalkyl, halogen, haloalkyl, hydroxy, alkoxy and aryloxy; and R$^{23}$ is selected from hydrogen, alkyl, alkenyl, alkynyl, halogen, heteroalkyl, haloalkyl, aryl, heteroaryl, cycloalkyl, and heterocycloalkyl; or $R^{21}$ and $R^{23}$, together with the atoms to which they are bonded, join to form an optionally substituted heterocyclic ring containing from 5 to 8 atoms of which 1 to 3 are heteroatoms; or $R^{20}$ and $R^{23}$, together with the atoms to which they are bonded, join to form an optionally substituted heterocyclic ring containing from 5 to 8 atoms of which 1 to 3 are heteroatoms;

or an optical isomer, diastereomer or enantiomer for Formula (I), or a pharmaceutically-acceptable salt, or biohydrolyzable amide, ester, or imide thereof.

2. The compound of claim 1 wherein l=0, 1 or 2.

3. The compound of claim 2, wherein E is selected from a covalent bond, —O— and —S—.

4. The compound of claim 3, wherein A is selected from lower alkyl, aryl, and heteroaryl.

5. The compound of claim 1 wherein Z is selected from —L—$(CR^{12}R^{12'})_a R^{13}$; —$NR^{15}R^{15'}$; and

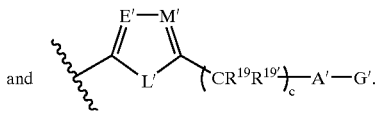

and

6. The compound of claim 5 wherein G' is —$(CR^{22}R^{22'})_e$—$R^{23}$ where e is 0 and $R^{23}$ is selected from alkyl, heteroalkyl, aryl, heteroaryl, cycloalkyl and heterocycloalkyl.

7. A compound having a structure according to Formula (I)

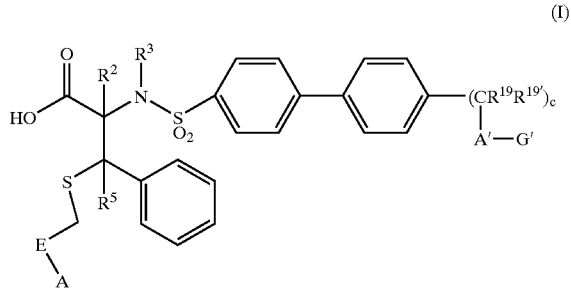

(I)

wherein:
- (A) $R^2$ is selected from hydrogen, lower alkyl, arylalkyl and heteroarylalkyl;
- (B) $R^3$ is selected from hydrogen, lower alkyl, arylalkyl and heteroarylalkyl;
- (C) l is from 0 to about 4;
- (D) E is selected from a covalent bond, —O—, —S—, —S(O)—, —S(O$_2$)—, —N($R^{10}$)—, —N(COR$^{10}$)—, —N(CO$_2$R$^{10}$)—, —N(CONR$^{10}$R$^{10'}$)—, and —N(SO$_2$R$^{10}$)—, where (i) each $R^{10}$ and $R^{10'}$, when present, is independently selected from hydrogen, alkyl, alkenyl, alkynyl, heteroalkyl, haloalkyl, aryl, arylalkyl, heteroaryl, heteroarylalkyl, cycloalkyl, and heterocycloalkyl, or (ii) $R^{10}$ and $R^{10'}$, together with the nitrogen atom to which they are bonded, join to form an optionally substituted heterocyclic ring containing from 5 to 8 ring atoms of which from 1 to 3 are heteroatoms; provided that when l=0, E is a covalent bond; and
- (E)
  - (1) A is selected from hydrogen, alkyl, alkenyl, alkynyl, heteroalkyl, haloalkyl, aryl, arylalkyl, heteroaryl, heteroarylalkyl, cycloalkyl, and heterocycloalkyl; or
  - (2) A, together with $R^{10}$, or $R^{10'}$, join to form an optionally substituted heterocyclic ring containing from 5 to 8 ring atoms of which from 1 to 3 are heteroatoms;
- (F) $R^5$ is selected from hydrogen, lower alkyl, arylalkyl and heteroarylalkyl;
- (G) c is from 0 to about 4;
- (H) each $R^{19}$ and $R^{19'}$, when present, is independently selected from hydrogen, alkyl, alkenyl, alkynyl, aryl, heteroalkyl, heteroaryl, cycloalkyl, heterocycloalkyl, halogen, haloalkyl, hydroxy, and alkoxy;
- (I) A' is selected from a covalent bond, —O—, —SO$_d$—, —C(O)—, —C(O)N($R^{21}$)—, —N($R^{21}$)—, and —N($R^{21}$)C(O)—; where d is from 0 to 2 and $R^{21}$ is selected from hydrogen, alkyl, alkenyl, alkynyl, aryl, heteroaryl, heteroalkyl, heteroaryl, cycloalkyl, heterocycloalkyl, and haloalkyl; and
- (J) G' is —$R^{23}$ and $R^{23}$ is selected from hydrogen, alkyl, heteroalkyl, aryl, heteroaryl, cycloalkyl, and heterocycloalkyl;

or an optical isomer, diastereomer or enantiomer for Formula (I), or a pharmaceutically-acceptable salt, or biohydrolyzable amide, ester, or imide thereof.

8. The compound of claim 7 wherein l=0, 1 or 2.

9. The compound of claim 8, wherein E is selected from a covalent bond, —O— and —S—.

10. The compound of claim 9, wherein A is selected from lower alkyl, aryl, and heteroaryl.

11. A compound having a structure according to Formula (I);

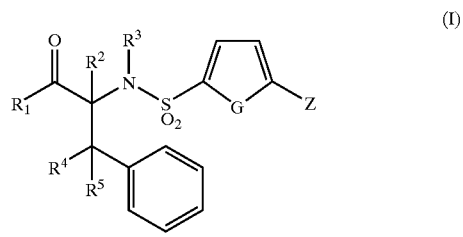

(I)

wherein:
- (A) $R^1$ is —OH;
- (B) $R^2$ is selected from hydrogen, lower alkyl, arylalkyl and heteroarylalkyl;
- (C) $R^3$ is selected from hydrogen, lower alkyl, arylalkyl and heteroarylalkyl;
- (D) $R^4$ is X—$(CR^8R^{8'})_l$—E—A where:
  - (1) X is —S—;
  - (2) each $R^8$ and $R^{8'}$, when present, is independently selected from hydrogen, alkyl, alkenyl, alkynyl, aryl, heteroalkyl, heteroaryl, cycloalkyl, heterocycloalkyl, halogen, and haloalkyl;
  - (3) l is from 0 to about 4;
  - (4) E is selected from a covalent bond, —O—, —S—, —S(O)—, —S(O$_2$)—, —N($R^{10}$)—, —N(COR$^{10}$)—, —N(CO$_2$R$^{10}$)—, —N(CONR$^{10}$R$^{10'}$)—, and —N(SO$_2$R$^{10}$)—, where (i) each $R^{10}$ and $R^{10'}$, when present, is independently selected from hydrogen, alkyl, alkenyl, alkynyl, heteroalkyl, haloalkyl, aryl, arylalkyl, heteroaryl, heteroarylalkyl, cycloalkyl, and heterocycloalkyl, or (ii) $R^{10}$ and $R^{10'}$, together with the nitrogen atom to which they are bonded, join to form an optionally substituted heterocyclic ring containing from 5 to 8 ring atoms of which from 1 to 3 are heteroatoms; provided that when l=0, E is a covalent bond;
(5)
  (a) A is selected from hydrogen, alkyl, alkenyl, alkynyl, heteroalkyl, haloalkyl, aryl, arylalkyl, heteroaryl, heteroarylalkyl, cycloalkyl, and heterocycloalkyl; or
  (b) A, together with $R^8$, $R^{8'}$, $R^{10}$, or $R^{10'}$, join to form an optionally substituted heterocyclic ring containing from 5 to 8 ring atoms of which from 1 to 3 are heteroatoms;
(E) $R^5$ is selected from hydrogen, lower alkyl, arylalkyl and heteroarylalkyl;
(F) G is selected from —C($R^{11}$)=C($R^{11'}$)—, where each $R^{11}$ and $R^{11'}$ is independently selected from hydrogen, alkyl, alkenyl, alkynyl, heteroalkyl, aryl, heteroaryl, cycloalkyl, and heterocycloalkyl;
(G) Z is selected from:
  (1) cycloalkyl and heterocycloalkyl;
  (2) —L—(C$R^{12}R^{12'}$)$_a$—$R^{13}$ where:
    (a) a is from 0 to about 4;
    (b) L is selected from —C≡C—, —CH=CH—, —N=N—, —O—, —S— and —SO$_2$—;
    (c) each $R^{12}$ and $R^{12'}$, when present, is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and
    (d) $R^{13}$ is selected from hydrogen, aryl, heteroaryl, alkyl, alkenyl, alkynyl, heteroalkyl, haloalkyl, heterocycloalkyl and cycloalkyl; and, if L is —C≡C— or —CH=CH—, then $R^{13}$ may also be selected from —CON($R^{14}R^{14'}$) where (i) $R^{14}$ and $R^{14'}$ are independently selected from hydrogen, alkyl, alkenyl, alkynyl, haloalkyl, heteroalkyl, aryl, heteroaryl, cycloalkyl, and heterocycloalkyl, or (ii) $R^{14}$ and $R^{14'}$, together with the nitrogen atom to which they are bonded, join to form an optionally substituted heterocyclic ring containing from 5 to 8 ring atoms of which from 1 to 3 are heteroatoms;
  (3) —N$R^{15}R^{15'}$ where:
    (a) $R^{15}$ and $R^{15'}$ each is independently selected from hydrogen, alkyl, alkenyl, alkynyl, heteroalkyl, haloalkyl, aryl, heteroaryl, cycloalkyl, heteroalkyl and —C(O)—Q—(C$R^{16}R^{16'}$)$_b$—$R^{17}$ where:
      (i) b is from 0 to about 4;
      (ii) Q is selected from a covalent bond and —N($R^{18}$)—; and
      (iii) each $R^{16}$ and $R^{16'}$, when present, is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; each $R^{17}$ and $R^{18}$ is independently selected from hydrogen, alkyl, alkenyl, alkynyl, heteroalkyl, haloalkyl, aryl, heteroaryl, cycloalkyl, and heterocycloalkyl, or $R^{17}$ and $R^{18}$, together with the atoms to which they are bonded, join to form an optionally substituted heterocyclic ring containing from 5 to 8 ring atoms of which from 1 to 3 are heteroatoms; or $R^{15}$ and $R^{18}$, together with the nitrogen atoms to which they are bonded, join to form an optionally substituted heterocyclic ring containing from 5 to 8 ring atoms of which from 2 to 3 are heteroatoms; or
    (b) $R^{15}$ and $R^{15'}$, together with the nitrogen atom to which they are bonded, join to form an optionally substituted heterocyclic ring containing from 5 to 8 ring atoms of which from 1 to 3 are heteroatoms; and (4)

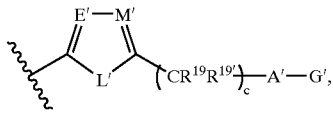

where:
  (a) E' and M' are independently selected from —CH— and —N—;
  (b) L' is selected from —S—, —O—, —N($R^{20}$)—, —C($R^{20}$)=C($R^{20'}$)—, —N=C($R^{20}$)—, and —N=N—, where each $R^{20}$ and $R^{20'}$, when present, is independently selected from hydrogen, alkyl, alkenyl, alkynyl, heteroalkyl, aryl, heteroaryl, cycloalkyl, and heterocycloalkyl;
  (c) c is from 0 to about 4;
  (d) each $R^{19}$ and $R^{19'}$, when present, is independently selected from hydrogen, alkyl, alkenyl, alkynyl, aryl, heteroalkyl, heteroaryl, cycloalkyl, heterocycloalkyl, halogen, haloalkyl, hydroxy, and alkoxy;
  (e) A' is selected from a covalent bond, —O—, —SO$_d$—, —C(O)—, —C(O)N($R^{21}$)—, —N($R^{21}$)—, and —N($R^{21}$)C(O)—; where d is from 0 to 2 and $R^{21}$ is selected from hydrogen, alkyl, alkenyl, alkynyl, aryl, heteroaryl, heteroalkyl, heteroaryl, cycloalkyl, heterocycloalkyl, and haloalkyl; and
  (f) G' is —$R^{23}$ and $R^{23}$ is selected from hydrogen, alkyl, heteroalkyl, aryl, heteroaryl, cycloalkyl, and heterocycloalkyl;
or an optical isomer, diastereomer or enantiomer for Formula (I), or a pharmaceutically-acceptable salt, or biohydrolyzable amide, ester, or imide thereof.

12. The compound of claim 11, wherein E is selected form a covalent bond, —O— and —S—.

13. The compound of claim 12, wherein A is selected from lower alkyl, aryl, and heteroaryl.

14. The compound of claim 11 selected from the group consisting of:
  (2S,3R)-3-Ethylsulfanyl-2-(4'-fluoro-biphenyl-4-sulfonylamino)-3-phenyl-propionic acid,
  (2S,3R)-3-Ethylsulfanyl-2-(4'-methoxy-biphenyl-4-sulfonylamino)-3-phenyl-propionic acid,
  (2S,3R)-2-(4'-Methoxy-biphenyl-4-sulfonylamino)-3-methylsulfanyl-3-phenyl-propionic acid
  (2S,3R)-2-(4'-Methoxy-biphenyl-4-sulfonylamino)-3-phenyl-3-phenylsulfanyl-propionic acid,
  (2S,3R)-2-(4'-Bromo-biphenyl-4-sulfonylamino)-3-phenyl-3-(pyridin-3-ylsulfanyl)-propionic acid,
  (2S,3R)-2-(4'-Bromo-biphenyl-4-sulfonylamino)-3-phenyl-3-(pyrimidin-2-ylsulfanyl)-propionic acid,
  (2S,3R)-3-(4-Fluoro-phenylsulfanyl)-2-(4'-methoxy-biphenyl-4-sulfonylamino)-3-phenyl-propionic acid,
  (2S,3R)-2-(4'-Methoxy-biphenyl-4-sulfonylamino)-3-phenyl-3-(thiazol-2-ylsulfanyl)-propionic acid,
  (2S,3R)-2-(4'-Methoxy-biphenyl-4-sulfonylamino)-3-methyl-1H-imidazol-2-ylsulfanyl)-3-phenyl-propionic acid,
  (2S,3R)-2-(4'-Chloro-biphenyl-4-sulfonylamino)-3-(oxazol-2-ylsulfanyl)-3-phenyl-propionic acid, (2S,3R)-2-(4'-Methylsulfanyl-biphenyl-4-sulfonylamino)-3-(1-methyl-1H-[1,2,4]triazol-3-ylsulfanyl)-3-phenyl-propionic acid, (2S, 3R)-2-(4'-Methoxy-biphenyl-4-sulfonylamino)-3-(1-methyl-1H-[1,2,4]triazol-3-ylsulfanyl)-3-phenyl-propionic acid, (2S,3R)-2-[Benzyl-(4'-methoxy-biphenyl-4-sulfonyl)-amino]-3-phenyl-3-phenylsulfanyl-propionic acid, (2S,3R)-3-Benzylsulfanyl-2-(biphenyl-4-sulfonylamino)-3-phenyl-propionic acid, (2S,3R)-3-Benzylsulfanyl-2-(4'-methoxy-biphenyl-4-sulfonylamino)-3-phenyl-propionic acid, (2S,3R)-2-(Biphenyl-4-sulfonylamino)-3-phenethylsulfanyl-3-phenyl-propionic acid, (2S,3R)-3-(4-Methyl-benzylsulfanyl)-3-phenyl-2-(4'-trifluoromethyl-biphenyl-4-sulfonylamino)-propionic acid, (2S,3R)-3-(4-Methoxy-benzylsulfanyl)-2-(4'-methyl-biphenyl-4-sulfonylamino)-3-phenyl-propionic acid, (2S,3R)-3-(4-Fluoro-benzylsulfanyl)-2-(4'-methoxy-biphenyl-4-sulfonylamino)-3-phenyl-propionic acid.

(2S,3R)-3-(2,4-Difluoro-benzylsulfanyl)-2-(4'-methoxy-biphenyl-4-sulfonylamino)-3-phenyl-propionic acid, (2S,3R)-2-(4'-Methylsulfanyl-biphenyl-4-sulfonylamino)-3-phenyl-3-(pyridin-4-ylmethylsulfanyl)-propionic acid, (2S,3R)-2-[(4'-Methoxy-biphenyl-4-sulfonyl)-methyl-amino]-3-phenyl-3-pyridin-3-ylmethylsulfanyl)-propionic acid, (2S3R)-2-(4'-Methoxy-biphenyl-4-sulfonylamino)-3-phenyl-3(pyridin-2-ylmethylsulfanyl)-propionic acid, (2S,3R)-2-(4'-Methoxy-biphenyl-4-sulfonylamino)-3-(5-methyl-oxazol-2-ylmethylsulfanyl)-3-phenyl-propionic acid, (2S,3R)-3-(Benzothiazol-2-ylsulfanyl)-2-(4'-methoxy-biphenyl-4-sulfonylamino)-3-phenyl-propionic acid, (2S,3R)-3-(2-tert-Butoxycarbonylamino-ethylsulfanyl)-2-(4'-methoxy-biphenyl-4-sulfonylamino)-3-phenyl-propionic acid, (2S,3R)-3-(2-Acetylamino-ethylsulfanyl)-2-(4'-methoxy-biphenyl-4-sulfonylamino)-3-phenyl-propionic acid, (2S,3R)-3-[2-(Methanesulfonyl-pyrdin-3-yl-amino)-ethylsulfanyl]-2-(4'-methoxy-biphenyl-4-sulfonylamino)-3-phenyl-propionic acid, (2S,3R)-2-(4'-Bromo-biphenyl-4-sulfonylamino)-3-[2-(methanesulfonyl-pyridin-3-yl-amino)-ethylsulfanyl]-3-phenyl-propionic acid, (2S,3R)-3-(2-Benzyloxy-ethylsulfanyl)-2-(4'-methoxy-biphenyl-4-sulfonylamino)-3-phenyl-propionic acid, (2S,3R)-2-(4'-Bromo-biphenyl-4-sulfonylamino)-3-(2-phenoxy-ethylsulfanyl)-3-phenyl-propionic acid, (2S,3R)-2-(4'-Methoxy-biphenyl-4-sulfonylamino)-3-(2-phenoxy-ethylsulfanyl)-3-phenyl-propionic acid, (2S,3R)-3-[2-(4-Fluoro-phenoxy)-ethylsulfanyl]-3-phenyl-2-(4'-trifluoromethyl-biphenyl-4-sulfonylamino)-propionic acid, (2S,3R)-3-Ethylsulfanyl-2-[4-(4-methoxy-phenylethynyl)-benzenesulfonylamino]-3-phenyl-propionic acid, (2S,3R)-3-Ethylsulfanyl-2-[4-(4-methoxy-benzoylamino)-benzenesulfonylamino]-3-phenyl-propionic acid, (2R,3S)-2-(4'-Methoxy-biphenyl-4-sulfonylamino)-3-methylsulfanyl-3-phenyl-propionic acid, (2R,3S)-3-Ethylsulfanyl-2-(4'-methoxy-biphenyl-4-sulfonylamino)-3-phenyl-propionic acid, (2R,3S)-2-(4'-Methoxy-biphenyl-4-sulfonylamimo)-3-phenyl-3-phenylsulfanyl)-propionic acid, and (2R,3S)-3-Benzylsulfanyl-2-(4'-methoxy-biphenyl-4-sulfonylamino)-3-phenyl-propionic acid.

15. A pharmaceutical composition comprising:

(a) a safe and effective amount of a compound of claim 1, 7, 11, or 14; and (b) a pharmaceutically-acceptable carrier.

* * * * *